United States Patent
Sun et al.

(12)

(10) Patent No.: US 6,635,481 B1
(45) Date of Patent: Oct. 21, 2003

(54) TBX3 GENE AND METHODS OF USING IT

(75) Inventors: Zairen Sun, Rockville, MD (US); Wufang Fan, Germantown, MD (US)

(73) Assignee: OriGene Technologies, Inc., Rockville, MD (US)

( * ) Notice: Subject to any disclaimer, the term of this patent is extended or adjusted under 35 U.S.C. 154(b) by 0 days.

(21) Appl. No.: 10/028,272

(22) Filed: Dec. 28, 2001

(51) Int. Cl.[7] .......................... C12N 5/00; C12N 15/00; C12P 21/06; C07H 21/04
(52) U.S. Cl. ................... 435/325; 435/320.1; 435/69.1; 536/23.5
(58) Field of Search ................ 530/350; 430/320.1, 430/325

(56) References Cited

PUBLICATIONS

He. M. et al. Transcription repression by Xenopus ET and its human ortholog TBX3, a gene involved in ulnar–mammary syndrome, Proc. Natl. Acad. Sci. U.S.A., 1999, 96,10212–10217.*

Bamshad M. et al. Mutations in human TBX3 alter limb, apocrine and genital development in ulnary–mammary syndrome, Nat. Genetics, 1997, 16, 311–315.*

* cited by examiner

*Primary Examiner*—Rebecca E. Prouty
*Assistant Examiner*—Malgorzata Walicka
(74) *Attorney, Agent, or Firm*—Richard M. Lebovitz

(57) ABSTRACT

The present invention relates to all facets of a novel polynucleotide, Tbx3-pr408, the polypeptides it encodes, antibodies and specific binding partners thereto, and their applications to research, diagnosis, drug discovery, therapy, clinical medicine, forensic science and medicine, etc. The polynucleotides useful in variety of ways, including, but not limited to, as molecular markers, as drug targets, and for detecting, diagnosing, staging, monitoring, prognosticating, preventing or treating, determining predisposition to, etc., diseases and conditions, such as mammary-ulnar syndrome and other developmental disorders.

5 Claims, 2 Drawing Sheets

FIG. 1A

```
              *         620         *         640         *         660
PR0408    : ░░░░░░░░░░░░░░░░░░░░░░░░░░░░░░░░░░░░░░RPRLRYSPYSIP░P░PDGSSLLTTA░ : 640
NM_005996 : ░░░░░░░░░░░░░░░░░░LRQPQLRC-TA░L░░░░░░░░RPRLRYSP░SI░░P░PDGSSLLTTA░ : 639
XM_016321 : ░░░░░░░░░░░░░░░░░░░░░░░░░░░░░░░░░░░░░░RPRLRYSPYSIP░P░PDGSSLLTTA░ : 660
NM_016569 : ------------------R░░░░░░-R░░░░░░░░RPRLRYSP░SIP░P░PDGSSL░TTA░ : 530

*         680         *         700         *         720
PR0408    : ░S░░░░░░░░░░░░░LAASPAS░A░DSGSE░NSPSSTLSSSS░S░SP░LCAEKEAATSE : 700
NM_005996 : ░░░░░░░░░░░░░░░░AASPAS░A░DSG░░P░░RSSTLSSSS░SLSP░LCAEKEAATSE : 699
XM_016321 : ░S░░░░░░░░░░░░░A░LAASPAS░A░DSGSE░░SPSSTLSSSS░S░SP░LCAEKEAATSE : 720
NM_016569 : ----------------░ASPAS░A░D░GSE░░SRSSTLSSSS░SLS░░LCA░KEAATSE : 573

*         740         *         760         *         780
PR0408    : ░QS░QP░VS░░░░A░PD░SR SASF-------------------------------- : 723
NM_005996 : ░QS░QP░VS░░░░A KPDRSR SASF-------------------------------- : 722
XM_016321 : ░QS░QP░VS░░░░A░PDRSR SASF-------------------------------- : 743
NM_016569 : ░QS░QP░VSG░░A░PDRSR SASF-------------------------------- : 596
```

FIG. 1B

SEQUENCE LISTING

```
<160> NUMBER OF SEQ ID NOS: 5

<210> SEQ ID NO 1
<211> LENGTH: 3113
<212> TYPE: DNA
<213> ORGANISM: Homo sapiens
<220> FEATURE:
<221> NAME/KEY: CDS
<222> LOCATION: (524)..(2695)
<223> OTHER INFORMATION:

<400> SEQUENCE: 1
caccagcgag aaagagggag aggaagacag ataggggcg ggggaagaag aaaaagaaag      60
gtaaaaagtc ttctaggaga acctttcaca tttgcaacaa aagacctagg ggctggagag    120
agattcctgg gacgcagggc tggagtgtct atttcgagct cagcggcagg gctcgggcgc    180
gagtcgagac cctgctcgct cctctcgctt ctgaaaccga cgttcaggag cggcttttta    240
aaaacgcaag gcacaaggac ggtcacccgc gcgactatgt ttgctgattt ttcgccttgc    300
cctctttaaa agcggcctcc cattcccaa aagacacttc ccctcctccc tttgaagtgc     360
attagttgtg atttctgcct cctttctttt tttctttctt ttttgttttg cttttccccc    420 cctttgaat tatgtgctgc tgttaaacaa caacaaaaaa acaacaaaac acagcagctg     480
cggacttgtc cccggctgga gcccagcgcc ccgcctggag tgg atg agc ctc tcc      535
                                                Met Ser Leu Ser
                                                 1 atg aga gat ccg gtc att cct ggg aca agc atg gcc tac cat ccg ttc      583
Met Arg Asp Pro Val Ile Pro Gly Thr Ser Met Ala Tyr His Pro Phe
 5              10                  15                  20 cta cct cac cgg gcg ccg gac ttc gcc atg agc gcg gtg ctg ggt cac      631
Leu Pro His Arg Ala Pro Asp Phe Ala Met Ser Ala Val Leu Gly His
             25                  30                  35 cag ccg ccg ttc ttc ccc gcg ctg acg ctg cct ccc aac ggc gcg gcg      679
Gln Pro Pro Phe Phe Pro Ala Leu Thr Leu Pro Pro Asn Gly Ala Ala
         40                  45                  50
```

-continued

| | |
|---|---|
| gcg ctc tcg ctg ccg ggc gcc ctg gcc aag ccg atc atg gat caa ttg<br>Ala Leu Ser Leu Pro Gly Ala Leu Ala Lys Pro Ile Met Asp Gln Leu<br>55                   60                   65 | 727 |
| gtg ggg gcg gcc gag acc ggc atc ccg ttc tcc tcc ctg ggg ccc cag<br>Val Gly Ala Ala Glu Thr Gly Ile Pro Phe Ser Ser Leu Gly Pro Gln<br>70                     75                   80 | 775 |
| gcg cat ctg agg cct ttg aag acc atg gag ccc gaa gaa gag gtg gag<br>Ala His Leu Arg Pro Leu Lys Thr Met Glu Pro Glu Glu Glu Val Glu<br>85                    90                   95                 100 | 823 |
| gac gac ccc aag gtg cac ctg gag gct aaa gaa ctt tgg gat cag ttt<br>Asp Asp Pro Lys Val His Leu Glu Ala Lys Glu Leu Trp Asp Gln Phe<br>                   105                 110                 115 | 871 |
| cac aag cgg ggc acc gag atg gtc att acc aag tcg gga agg cga atg<br>His Lys Arg Gly Thr Glu Met Val Ile Thr Lys Ser Gly Arg Arg Met<br>          120                 125                 130 | 919 |
| ttt cct cca ttt aaa gtg aga tgt tct ggg ctg gat aaa aaa gcc aaa<br>Phe Pro Pro Phe Lys Val Arg Cys Ser Gly Leu Asp Lys Lys Ala Lys<br>         135                 140                 145 | 967 |
| tac att tta ttg atg gac att ata gct gct gat gac tgt cgt tat aaa<br>Tyr Ile Leu Leu Met Asp Ile Ile Ala Ala Asp Asp Cys Arg Tyr Lys<br>150                   155                 160 | 1015 |
| ttt cac aat tct cgg tgg atg gtg gct ggt aag gcc gac ccc gaa atg<br>Phe His Asn Ser Arg Trp Met Val Ala Gly Lys Ala Asp Pro Glu Met<br>165                   170                 175                 180 | 1063 |
| cca aag agg atg tac att cac ccg gac agc ccc gct act ggg gaa cag<br>Pro Lys Arg Met Tyr Ile His Pro Asp Ser Pro Ala Thr Gly Glu Gln<br>                   185                 190                 195 | 1111 |
| tgg atg tcc aaa gtc gtc act ttc cac aaa ctg aaa ctc acc aac aac<br>Trp Met Ser Lys Val Val Thr Phe His Lys Leu Lys Leu Thr Asn Asn<br>         200                 205                 210 | 1159 |
| att tca gac aaa cat gga ttt act ata ttg aac tcc atg cac aaa tac<br>Ile Ser Asp Lys His Gly Phe Thr Ile Leu Asn Ser Met His Lys Tyr<br>         215                 220                 225 | 1207 |
| cag ccc cgg ttc cac att gta aga gcc aat gac atc ttg aaa ctc cct<br>Gln Pro Arg Phe His Ile Val Arg Ala Asn Asp Ile Leu Lys Leu Pro<br>230                   235                 240 | 1255 |
| tat agt aca ttt cgg aca tac ttg ttc ccc gaa act gaa ttc atc gct<br>Tyr Ser Thr Phe Arg Thr Tyr Leu Phe Pro Glu Thr Glu Phe Ile Ala<br>245                   250                 255                 260 | 1303 |
| gtg act gca tac cag aat gat aag ata acc cag tta aaa ata gac aac<br>Val Thr Ala Tyr Gln Asn Asp Lys Ile Thr Gln Leu Lys Ile Asp Asn<br>                   265                 270                 275 | 1351 |
| aac cct ttt gca aaa ggt ttc cgg gac act gga aat ggc cga aga gaa<br>Asn Pro Phe Ala Lys Gly Phe Arg Asp Thr Gly Asn Gly Arg Arg Glu<br>                   280                 285                 290 | 1399 |
| aaa aga aaa cag ctc acc ctg cag tcc atg agg gtg ttt gat gaa aga<br>Lys Arg Lys Gln Leu Thr Leu Gln Ser Met Arg Val Phe Asp Glu Arg<br>295                   300                 305 | 1447 |
| cac aaa aag gag aat ggg acc tct gat gag tcc tcc agt gaa caa gca<br>His Lys Lys Glu Asn Gly Thr Ser Asp Glu Ser Ser Ser Glu Gln Ala<br>310                   315                 320 | 1495 |
| gct ttc aac tgc ttc gcc cag gct tct tct cca gcc gcc tcc act gta<br>Ala Phe Asn Cys Phe Ala Gln Ala Ser Ser Pro Ala Ala Ser Thr Val<br>325                   330                 335                 340 | 1543 |
| ggg aca tcg aac ctc aaa gat tta tgt ccc agc gag ggt gag agc gac<br>Gly Thr Ser Asn Leu Lys Asp Leu Cys Pro Ser Glu Gly Glu Ser Asp<br>                   345                 350                 355 | 1591 |
| gcc gag gcc gag agc aaa gag gag cat ggc ccc gag gcc tgc gac gcg<br>Ala Glu Ala Glu Ser Lys Glu Glu His Gly Pro Glu Ala Cys Asp Ala<br>         360                 365                 370 | 1639 |

```
gcc aag atc tcc acc acc acg tcg gag gag ccc tgc cgt gac aag ggc     1687
Ala Lys Ile Ser Thr Thr Thr Ser Glu Glu Pro Cys Arg Asp Lys Gly
            375                 380                 385 agc ccc gcg gtc aag gct cac ctt ttc gct gct gag cgg ccc cgg gac     1735
Ser Pro Ala Val Lys Ala His Leu Phe Ala Ala Glu Arg Pro Arg Asp
        390                 395                 400 agc ggg cgg ctg gac aaa gcg tcg ccc gac tca cgc cat agc ccc gcc     1783
Ser Gly Arg Leu Asp Lys Ala Ser Pro Asp Ser Arg His Ser Pro Ala
405                 410                 415                 420 acc atc tcg tcc agc act cgc ggc ctg ggc gcg gag gag cgc agg agc     1831
Thr Ile Ser Ser Ser Thr Arg Gly Leu Gly Ala Glu Glu Arg Arg Ser
                425                 430                 435 ccg gtt cgc gag ggc aca gcg ccg gcc aag gtg gaa gag gcg cgc gcg     1879
Pro Val Arg Glu Gly Thr Ala Pro Ala Lys Val Glu Glu Ala Arg Ala
            440                 445                 450 ctc ccg ggc aag gag gcc ttc gcg ccg ctc acg gtg cag acg gac gcg     1927
Leu Pro Gly Lys Glu Ala Phe Ala Pro Leu Thr Val Gln Thr Asp Ala
        455                 460                 465 gcc gcc gcg cac ctg gcc cag ggc ccc ctg cct ggc ctc ggc ttc gcc     1975
Ala Ala Ala His Leu Ala Gln Gly Pro Leu Pro Gly Leu Gly Phe Ala
470                 475                 480 ccg ggc ctg gcg ggc caa cag ttc ttc aac ggg cac ccg ctc ttc ctg     2023
Pro Gly Leu Ala Gly Gln Gln Phe Phe Asn Gly His Pro Leu Phe Leu
485                 490                 495                 500 cac ccc agc cag ttt gcc atg ggg ggc gcc ttc tcc agc atg gcg gcc     2071
His Pro Ser Gln Phe Ala Met Gly Gly Ala Phe Ser Ser Met Ala Ala
            505                 510                 515 gct ggc atg ggt ccc ctc ctg gcc acg gtt tct ggg gcc tcc acc ggt     2119
Ala Gly Met Gly Pro Leu Leu Ala Thr Val Ser Gly Ala Ser Thr Gly
        520                 525                 530 gtc tcg ggc ctg gat tcc acg gcc atg gcc tct gcc gct gcg gcg cag     2167
Val Ser Gly Leu Asp Ser Thr Ala Met Ala Ser Ala Ala Ala Ala Gln
    535                 540                 545 gga ctg tcc ggg gcg tcc gcg gcc acc ctg ccc ttc cac ctc cag cag     2215
Gly Leu Ser Gly Ala Ser Ala Ala Thr Leu Pro Phe His Leu Gln Gln
550                 555                 560 cac gtc ctg gcc tct cag ggc ctg gcc atg tcc cct ttc gga agc ctg     2263
His Val Leu Ala Ser Gln Gly Leu Ala Met Ser Pro Phe Gly Ser Leu
565                 570                 575                 580 ttc cct tac ccc tac acg tac atg gca gca gcg gcg gcc gcc tcc tct     2311
Phe Pro Tyr Pro Tyr Thr Tyr Met Ala Ala Ala Ala Ala Ala Ser Ser
            585                 590                 595 gcg gca gcc tcc agc tcg gtg cac cgc cac ccc ttc ctc aat ctg aac     2359
Ala Ala Ala Ser Ser Ser Val His Arg His Pro Phe Leu Asn Leu Asn
        600                 605                 610 acc atg cgc ccg cgg ctg cgc tac agc ccc tac tcc atc ccg gtg ccg     2407
Thr Met Arg Pro Arg Leu Arg Tyr Ser Pro Tyr Ser Ile Pro Val Pro
            615                 620                 625 gtc ccg gac ggc agc agt ctg ctc acc acc gcc ctg ccc tcc atg gcg     2455
Val Pro Asp Gly Ser Ser Leu Leu Thr Thr Ala Leu Pro Ser Met Ala
        630                 635                 640 gcg gcc gcg ggg ccc ctg gac ggc aaa gtc gcc gcc ctg gcc gcc agc     2503
Ala Ala Ala Gly Pro Leu Asp Gly Lys Val Ala Ala Leu Ala Ala Ser
645                 650                 655                 660 ccg gcc tcg gtg gca gtg gac tcg ggc tct gaa ctc aac agc cgc tcc     2551
Pro Ala Ser Val Ala Val Asp Ser Gly Ser Glu Leu Asn Ser Arg Ser
                665                 670                 675 tcc acg ctc tcc tcc agc tcc atg tcc ttg tcg ccc aaa ctc tgc gcg     2599
Ser Thr Leu Ser Ser Ser Ser Met Ser Leu Ser Pro Lys Leu Cys Ala
```

|   |   |   |   |   | 680 |   |   |   |   | 685 |   |   |   |   | 690 |   |   |   |
|---|---|---|---|---|---|---|---|---|---|---|---|---|---|---|---|---|---|---|
| gag | aaa | gag | gcg | gcc | acc | agc | gaa | ctg | cag | agc | atc | cag | cgg | ttg | gtt | | | 2647 |
| Glu | Lys | Glu | Ala | Ala | Thr | Ser | Glu | Leu | Gln | Ser | Ile | Gln | Arg | Leu | Val | | | |
|   |   |   |   | 695 |   |   |   |   | 700 |   |   |   |   | 705 |   |   |   |   |

| agc | ggc | ttg | gaa | gcc | aag | ccg | gac | agg | tcc | cgc | agc | gcg | tcc | ccg | tag | 2695 |
|---|---|---|---|---|---|---|---|---|---|---|---|---|---|---|---|---|
| Ser | Gly | Leu | Glu | Ala | Lys | Pro | Asp | Arg | Ser | Arg | Ser | Ala | Ser | Pro | | |
|   | 710 |   |   |   |   | 715 |   |   |   |   | 720 |   |   |   |   |   | acccgtccca gacacgtctt ttcattccag tccagttcag gctgccgtgc actttgtcgg 2755 atataaaata aaccacgggc cgccatggc gttagccctt cctttttgcag ttgcgtctgg 2815 gaagggcccc cggactccct cgagagaatg tgctagagac agcccctgtc ttcttggcgt 2875 ggtttatatg tccgggatct ggatcagatt ctgggggctc agaaacgtcg gttgcattga 2935 gctactgggg gtaggagttc caacatttat gtccagagca acttccagca aggctggtct 2995 gggtctctgc ccaccaggcg gggaggtgtt caaagacatc tccctcagtg cggatttata 3055 tatatatttt tccttcactg tgtcaagtgg aaacaaaaac aaaaaaaaaa aaaaaaaa 3113

<210> SEQ ID NO 2
<211> LENGTH: 723
<212> TYPE: PRT
<213> ORGANISM: Homo sapiens

<400> SEQUENCE: 2

Met Ser Leu Ser Met Arg Asp Pro Val Ile Pro Gly Thr Ser Met Ala
1               5                  10                  15

Tyr His Pro Phe Leu Pro His Arg Ala Pro Asp Phe Ala Met Ser Ala
                20                  25                  30

Val Leu Gly His Gln Pro Pro Phe Phe Pro Ala Leu Thr Leu Pro Pro
            35                  40                  45

Asn Gly Ala Ala Ala Leu Ser Leu Pro Gly Ala Leu Ala Lys Pro Ile
        50                  55                  60

Met Asp Gln Leu Val Gly Ala Ala Glu Thr Gly Ile Pro Phe Ser Ser
65                  70                  75                  80

Leu Gly Pro Gln Ala His Leu Arg Pro Leu Lys Thr Met Glu Pro Glu
                85                  90                  95

Glu Glu Val Glu Asp Asp Pro Lys Val His Leu Glu Ala Lys Glu Leu
            100                 105                 110

Trp Asp Gln Phe His Lys Arg Gly Thr Glu Met Val Ile Thr Lys Ser
        115                 120                 125

Gly Arg Arg Met Phe Pro Pro Phe Lys Val Arg Cys Ser Gly Leu Asp
    130                 135                 140

Lys Lys Ala Lys Tyr Ile Leu Leu Met Asp Ile Ile Ala Ala Asp Asp
145                 150                 155                 160

Cys Arg Tyr Lys Phe His Asn Ser Arg Trp Met Val Ala Gly Lys Ala
                165                 170                 175

Asp Pro Glu Met Pro Lys Arg Met Tyr Ile His Pro Asp Ser Pro Ala
            180                 185                 190

Thr Gly Glu Gln Trp Met Ser Lys Val Val Thr Phe His Lys Leu Lys
        195                 200                 205

Leu Thr Asn Asn Ile Ser Asp Lys His Gly Phe Thr Ile Leu Asn Ser
    210                 215                 220

Met His Lys Tyr Gln Pro Arg Phe His Ile Val Arg Ala Asn Asp Ile
225                 230                 235                 240

Leu Lys Leu Pro Tyr Ser Thr Phe Arg Thr Tyr Leu Phe Pro Glu Thr
                245                 250                 255

```
Glu Phe Ile Ala Val Thr Ala Tyr Gln Asn Asp Lys Ile Thr Gln Leu
                260                 265                 270
Lys Ile Asp Asn Asn Pro Phe Ala Lys Gly Phe Arg Asp Thr Gly Asn
            275                 280                 285
Gly Arg Arg Glu Lys Arg Lys Gln Leu Thr Leu Gln Ser Met Arg Val
        290                 295                 300
Phe Asp Glu Arg His Lys Lys Glu Asn Gly Thr Ser Asp Glu Ser Ser
305                 310                 315                 320
Ser Glu Gln Ala Ala Phe Asn Cys Phe Ala Gln Ala Ser Ser Pro Ala
                325                 330                 335
Ala Ser Thr Val Gly Thr Ser Asn Leu Lys Asp Leu Cys Pro Ser Glu
            340                 345                 350
Gly Glu Ser Asp Ala Glu Ala Glu Ser Lys Glu Glu His Gly Pro Glu
        355                 360                 365
Ala Cys Asp Ala Ala Lys Ile Ser Thr Thr Thr Ser Glu Glu Pro Cys
            370                 375                 380
Arg Asp Lys Gly Ser Pro Ala Val Lys Ala His Leu Phe Ala Ala Glu
385                 390                 395                 400
Arg Pro Arg Asp Ser Gly Arg Leu Asp Lys Ala Ser Pro Asp Ser Arg
                405                 410                 415
His Ser Pro Ala Thr Ile Ser Ser Thr Arg Gly Leu Gly Ala Glu
            420                 425                 430
Glu Arg Arg Ser Pro Val Arg Glu Gly Thr Ala Pro Ala Lys Val Glu
                435                 440                 445
Glu Ala Arg Ala Leu Pro Gly Lys Glu Ala Phe Ala Pro Leu Thr Val
450                 455                 460
Gln Thr Asp Ala Ala Ala His Leu Ala Gln Gly Pro Leu Pro Gly
465                 470                 475                 480
Leu Gly Phe Ala Pro Gly Leu Ala Gly Gln Gln Phe Phe Asn Gly His
                485                 490                 495
Pro Leu Phe Leu His Pro Ser Gln Phe Ala Met Gly Gly Ala Phe Ser
            500                 505                 510
Ser Met Ala Ala Ala Gly Met Gly Pro Leu Leu Ala Thr Val Ser Gly
        515                 520                 525
Ala Ser Thr Gly Val Ser Gly Leu Asp Ser Thr Ala Met Ala Ser Ala
530                 535                 540
Ala Ala Ala Gln Gly Leu Ser Gly Ala Ser Ala Ala Thr Leu Pro Phe
545                 550                 555                 560
His Leu Gln Gln His Val Leu Ala Ser Gln Gly Leu Ala Met Ser Pro
                565                 570                 575
Phe Gly Ser Leu Phe Pro Tyr Pro Tyr Thr Tyr Met Ala Ala Ala Ala
            580                 585                 590
Ala Ala Ser Ser Ala Ala Ala Ser Ser Val His Arg His Pro Phe
        595                 600                 605
Leu Asn Leu Asn Thr Met Arg Pro Arg Leu Arg Tyr Ser Pro Tyr Ser
            610                 615                 620
Ile Pro Val Pro Val Pro Asp Gly Ser Ser Leu Leu Thr Thr Ala Leu
625                 630                 635                 640
Pro Ser Met Ala Ala Ala Gly Pro Leu Asp Gly Lys Val Ala Ala
                645                 650                 655
Leu Ala Ala Ser Pro Ala Ser Val Ala Val Asp Ser Gly Ser Glu Leu
            660                 665                 670
```

```
Asn Ser Arg Ser Ser Thr Leu Ser Ser Ser Met Ser Leu Ser Pro
            675                 680                 685

Lys Leu Cys Ala Glu Lys Glu Ala Ala Thr Ser Glu Leu Gln Ser Ile
690                 695                 700

Gln Arg Leu Val Ser Gly Leu Glu Ala Lys Pro Asp Arg Ser Arg Ser
705                 710                 715                 720

Ala Ser Pro

<210> SEQ ID NO 3
<211> LENGTH: 722
<212> TYPE: PRT
<213> ORGANISM: Homo sapiens

<400> SEQUENCE: 3

Met Ser Leu Ser Met Arg Asp Pro Val Ile Pro Gly Thr Ser Met Ala
1               5                   10                  15

Tyr His Pro Phe Leu Pro His Arg Ala Pro Asp Phe Ala Met Ser Ala
                20                  25                  30

Val Leu Gly His Gln Pro Pro Phe Phe Pro Ala Leu Thr Leu Pro Pro
            35                  40                  45

Asn Gly Ala Ala Ala Leu Ser Leu Pro Gly Ala Leu Ala Lys Pro Ile
50                  55                  60

Met Asp Gln Leu Val Gly Ala Ala Glu Thr Gly Ile Pro Phe Ser Ser
65                  70                  75                  80

Leu Gly Pro Gln Ala His Leu Arg Pro Leu Lys Thr Met Glu Pro Glu
                85                  90                  95

Glu Glu Val Glu Asp Asp Pro Lys Val His Leu Glu Ala Lys Glu Leu
            100                 105                 110

Trp Asp Gln Phe His Lys Arg Gly Thr Glu Met Val Ile Thr Lys Ser
        115                 120                 125

Gly Arg Arg Met Phe Pro Pro Phe Lys Val Arg Cys Ser Gly Leu Asp
130                 135                 140

Lys Lys Ala Lys Tyr Ile Leu Leu Met Asp Ile Ile Ala Ala Asp Asp
145                 150                 155                 160

Cys Arg Tyr Lys Phe His Asn Ser Arg Trp Met Val Ala Gly Lys Ala
                165                 170                 175

Asp Pro Glu Met Pro Lys Arg Met Tyr Ile His Pro Asp Ser Pro Ala
            180                 185                 190

Thr Gly Glu Gln Trp Met Ser Lys Val Val Thr Phe His Lys Leu Lys
        195                 200                 205

Leu Thr Asn Asn Ile Ser Asp Lys His Gly Phe Thr Ile Leu Asn Ser
210                 215                 220

Met His Lys Tyr Gln Pro Arg Phe His Ile Val Arg Ala Asn Asp Ile
225                 230                 235                 240

Leu Lys Leu Pro Tyr Ser Thr Phe Arg Thr Tyr Leu Phe Pro Glu Thr
                245                 250                 255

Glu Phe Ile Ala Val Thr Ala Tyr Gln Asn Asp Lys Ile Thr Gln Leu
            260                 265                 270

Lys Ile Asp Asn Asn Pro Phe Ala Lys Gly Phe Arg Asp Thr Gly Asn
        275                 280                 285

Gly Arg Arg Glu Lys Arg Lys Gln Leu Thr Leu Gln Ser Met Arg Val
290                 295                 300

Phe Asp Glu Arg His Lys Lys Glu Asn Gly Thr Ser Asp Glu Ser Ser
305                 310                 315                 320
```

```
Ser Glu Gln Ala Ala Phe Asn Cys Phe Ala Gln Ala Ser Ser Pro Ala
                325                 330                 335

Ala Ser Thr Val Gly Thr Ser Asn Leu Lys Asp Leu Cys Pro Ser Glu
            340                 345                 350

Gly Glu Ser Asp Ala Glu Ala Glu Ser Lys Glu Glu His Gly Pro Glu
        355                 360                 365

Ala Cys Asp Ala Ala Lys Ile Ser Thr Thr Thr Ser Glu Glu Pro Cys
    370                 375                 380

Arg Asp Lys Gly Ser Pro Ala Val Lys Ala His Leu Phe Ala Ala Glu
385                 390                 395                 400

Arg Pro Arg Asp Ser Gly Arg Leu Asp Lys Ala Ser Pro Asp Ser Arg
                405                 410                 415

His Ser Pro Ala Thr Ile Ser Ser Thr Arg Gly Leu Gly Ala Glu
            420                 425                 430

Glu Arg Arg Ser Pro Val Arg Glu Gly Thr Ala Pro Ala Lys Val Glu
        435                 440                 445

Glu Ala Arg Ala Leu Pro Gly Lys Glu Ala Phe Ala Pro Leu Thr Val
    450                 455                 460

Gln Thr Asp Ala Ala Ala Ala His Leu Ala Gln Gly Pro Leu Pro Gly
465                 470                 475                 480

Leu Gly Phe Ala Pro Gly Leu Ala Gly Gln Gln Phe Phe Asn Gly His
                485                 490                 495

Pro Leu Phe Leu His Pro Ser Gln Phe Ala Met Gly Gly Ala Phe Ser
            500                 505                 510

Ser Met Ala Ala Ala Gly Met Gly Pro Leu Leu Ala Thr Val Ser Gly
        515                 520                 525

Ala Ser Thr Gly Val Ser Gly Leu Asp Ser Thr Ala Met Ala Ser Ala
    530                 535                 540

Ala Ala Ala Gln Gly Leu Ser Gly Ala Ser Ala Ala Thr Leu Pro Phe
545                 550                 555                 560

His Leu Gln Gln His Val Leu Ala Ser Gln Gly Leu Ala Met Ser Pro
                565                 570                 575

Phe Gly Ser Leu Phe Pro Tyr Pro Tyr Thr Tyr Met Ala Ala Ala Ala
            580                 585                 590

Ala Ala Ser Leu Arg Gln Pro Gln Leu Arg Cys Thr Ala Pro Leu Leu
        595                 600                 605

Asn Leu Asn Thr Met Arg Pro Arg Leu Arg Tyr Ser Pro Tyr Ser Ile
    610                 615                 620

Pro Val Pro Val Pro Asp Gly Ser Ser Leu Leu Thr Thr Ala Leu Pro
625                 630                 635                 640

Ser Met Ala Ala Ala Gly Pro Leu Asp Gly Lys Ala Ala Ala Leu
                645                 650                 655

Ala Ala Ser Pro Ala Ser Val Ala Val Asp Ser Gly Ser Glu Pro Asn
            660                 665                 670

Ser Arg Ser Ser Thr Leu Ser Ser Ser Met Ser Leu Ser Pro Lys
        675                 680                 685

Leu Cys Ala Glu Lys Glu Ala Ala Thr Ser Glu Leu Gln Ser Ile Gln
    690                 695                 700

Arg Leu Val Ser Gly Leu Glu Ala Lys Pro Asp Arg Ser Arg Ser Ala
705                 710                 715                 720

Ser Pro

<210> SEQ ID NO 4
```

-continued

```
<211> LENGTH: 743
<212> TYPE: PRT
<213> ORGANISM: Homo sapiens

<400> SEQUENCE: 4

Met Ser Leu Ser Met Arg Asp Pro Val Ile Pro Gly Thr Ser Met Ala
1               5                   10                  15

Tyr His Pro Phe Leu Pro His Arg Ala Pro Asp Phe Ala Met Ser Ala
            20                  25                  30

Val Leu Gly His Gln Pro Pro Phe Phe Pro Ala Leu Thr Leu Pro Pro
        35                  40                  45

Asn Gly Ala Ala Ala Leu Ser Leu Pro Gly Ala Leu Ala Lys Pro Ile
    50                  55                  60

Met Asp Gln Leu Val Gly Ala Ala Glu Thr Gly Ile Pro Phe Ser Ser
65                  70                  75                  80

Leu Gly Pro Gln Ala His Leu Arg Pro Leu Lys Thr Met Glu Pro Glu
                85                  90                  95

Glu Glu Val Glu Asp Asp Pro Lys Val His Leu Glu Ala Lys Glu Leu
            100                 105                 110

Trp Asp Gln Phe His Lys Arg Gly Thr Glu Met Val Ile Thr Lys Ser
        115                 120                 125

Gly Arg Arg Met Phe Pro Pro Phe Lys Val Arg Cys Ser Gly Leu Asp
    130                 135                 140

Lys Lys Ala Lys Tyr Ile Leu Leu Met Asp Ile Ile Ala Ala Asp Asp
145                 150                 155                 160

Cys Arg Tyr Lys Phe His Asn Ser Arg Trp Met Val Ala Gly Lys Ala
                165                 170                 175

Asp Pro Glu Met Pro Lys Arg Met Tyr Ile His Pro Asp Ser Pro Ala
            180                 185                 190

Thr Gly Glu Gln Trp Met Ser Lys Val Val Thr Phe His Lys Leu Lys
        195                 200                 205

Leu Thr Asn Asn Ile Ser Asp Lys His Gly Phe Thr Leu Ala Phe Pro
    210                 215                 220

Ser Asp His Ala Thr Trp Gln Gly Asn Tyr Ser Phe Gly Thr Gln Thr
225                 230                 235                 240

Ile Leu Asn Ser Met His Lys Tyr Gln Pro Arg Phe His Ile Val Arg
                245                 250                 255

Ala Asn Asp Ile Leu Lys Leu Pro Tyr Ser Thr Phe Arg Thr Tyr Leu
            260                 265                 270

Phe Pro Glu Thr Glu Phe Ile Ala Val Thr Ala Tyr Gln Asn Asp Lys
        275                 280                 285

Ile Thr Gln Leu Lys Ile Asp Asn Asn Pro Phe Ala Lys Gly Phe Arg
    290                 295                 300

Asp Thr Gly Asn Gly Arg Arg Glu Lys Arg Lys Gln Leu Thr Leu Gln
305                 310                 315                 320

Ser Met Arg Val Phe Asp Glu Arg His Lys Lys Glu Asn Gly Thr Ser
                325                 330                 335

Asp Glu Ser Ser Ser Glu Gln Ala Ala Phe Asn Cys Phe Ala Gln Ala
            340                 345                 350

Ser Ser Pro Ala Ala Ser Thr Val Gly Thr Ser Asn Leu Lys Asp Leu
        355                 360                 365

Cys Pro Ser Glu Gly Glu Ser Asp Ala Glu Ala Glu Ser Lys Glu Glu
    370                 375                 380

His Gly Pro Glu Ala Cys Asp Ala Ala Lys Ile Ser Thr Thr Thr Ser
```

```
385                 390                 395                 400

Glu Glu Pro Cys Arg Asp Lys Gly Ser Pro Ala Val Lys Ala His Leu
                405                 410                 415

Phe Ala Ala Glu Arg Pro Arg Asp Ser Gly Arg Leu Asp Lys Ala Ser
                420                 425                 430

Pro Asp Ser Arg His Ser Pro Ala Thr Ile Ser Ser Thr Arg Gly
            435                 440                 445

Leu Gly Ala Glu Glu Arg Arg Ser Pro Val Arg Glu Gly Thr Ala Pro
        450                 455                 460

Ala Lys Val Glu Glu Ala Arg Ala Leu Pro Gly Lys Glu Ala Phe Ala
465                 470                 475                 480

Pro Leu Thr Val Gln Thr Asp Ala Ala Ala His Leu Ala Gln Gly
                485                 490                 495

Pro Leu Pro Gly Leu Gly Phe Ala Pro Gly Leu Ala Gly Gln Gln Phe
            500                 505                 510

Phe Asn Gly His Pro Leu Phe Leu His Pro Ser Gln Phe Ala Met Gly
        515                 520                 525

Gly Ala Phe Ser Ser Met Ala Ala Gly Met Gly Pro Leu Leu Ala
                535                 540
    530

Thr Val Ser Gly Ala Ser Thr Gly Val Ser Gly Leu Asp Ser Thr Ala
545                 550                 555                 560

Met Ala Ser Ala Ala Ala Gln Gly Leu Ser Gly Ala Ser Ala Ala
                565                 570                 575

Thr Leu Pro Phe His Leu Gln Gln His Val Leu Ala Ser Gln Gly Leu
                580                 585                 590

Ala Met Ser Pro Phe Gly Ser Leu Phe Pro Tyr Pro Tyr Thr Tyr Met
        595                 600                 605

Ala Ala Ala Ala Ala Ser Ser Ala Ala Ser Ser Ser Val His
        610                 615                 620

Arg His Pro Phe Leu Asn Leu Asn Thr Met Arg Pro Arg Leu Arg Tyr
625                 630                 635                 640

Ser Pro Tyr Ser Ile Pro Val Pro Val Pro Asp Gly Ser Ser Leu Leu
                645                 650                 655

Thr Thr Ala Leu Pro Ser Met Ala Ala Ala Gly Pro Leu Asp Gly
                660                 665                 670

Lys Val Ala Ala Leu Ala Ala Ser Pro Ala Ser Val Ala Val Asp Ser
        675                 680                 685

Gly Ser Glu Leu Asn Ser Arg Ser Ser Thr Leu Ser Ser Ser Ser Met
    690                 695                 700

Ser Leu Ser Pro Lys Leu Cys Ala Glu Lys Glu Ala Ala Thr Ser Glu
705                 710                 715                 720

Leu Gln Ser Ile Gln Arg Leu Val Ser Gly Leu Glu Ala Lys Pro Asp
                725                 730                 735

Arg Ser Arg Ser Ala Ser Pro
                740

<210> SEQ ID NO 5
<211> LENGTH: 596
<212> TYPE: PRT
<213> ORGANISM: Homo sapiens

<400> SEQUENCE: 5

Met Ser Leu Ser Met Arg Asp Pro Val Ile Pro Gly Thr Ser Met Ala
1               5                   10                  15
```

```
Tyr His Pro Phe Leu Pro His Arg Ala Pro Asp Phe Ala Met Ser Ala
             20                  25                  30

Val Leu Gly His Gln Pro Pro Phe Phe Pro Ala Leu Thr Leu Pro Pro
             35                  40                  45

Asn Gly Ala Ala Ala Leu Ser Leu Pro Gly Ala Leu Ala Lys Pro Ile
 50                  55                  60

Met Asp Gln Leu Val Gly Ala Ala Glu Thr Gly Ile Pro Phe Ser Ser
 65                  70                  75                  80

Leu Gly Pro Gln Ala His Leu Arg Pro Leu Lys Thr Met Glu Pro Glu
                 85                  90                  95

Glu Glu Val Glu Asp Asp Pro Lys Val His Leu Glu Ala Lys Glu Leu
             100                 105                 110

Trp Asp Gln Phe His Lys Arg Gly Thr Glu Met Val Ile Thr Lys Ser
             115                 120                 125

Gly Arg Arg Met Phe Pro Pro Phe Lys Val Arg Cys Ser Gly Leu Asp
 130                 135                 140

Lys Lys Ala Lys Tyr Ile Leu Leu Met Asp Ile Ile Ala Ala Asp Asp
 145                 150                 155                 160

Cys Arg Tyr Lys Phe His Asn Ser Arg Trp Met Val Ala Gly Lys Ala
                 165                 170                 175

Asp Pro Glu Met Pro Lys Arg Met Tyr Ile His Pro Asp Ser Pro Ala
             180                 185                 190

Thr Gly Glu Gln Trp Met Ser Lys Val Val Thr Phe His Lys Leu Lys
             195                 200                 205

Leu Thr Asn Asn Ile Ser Asp Lys His Gly Phe Thr Leu Ala Phe Pro
 210                 215                 220

Ser Asp His Ala Thr Trp Gln Gly Asn Tyr Ser Phe Gly Thr Gln Thr
225                 230                 235                 240

Ile Leu Asn Ser Met His Lys Tyr Gln Pro Arg Phe His Ile Val Arg
                 245                 250                 255

Ala Asn Asp Ile Leu Lys Leu Pro Tyr Ser Thr Phe Arg Thr Tyr Leu
             260                 265                 270

Phe Pro Glu Thr Glu Phe Ile Ala Val Thr Ala Tyr Gln Asn Asp Lys
             275                 280                 285

Ile Thr Gln Leu Lys Ile Asp Asn Asn Pro Phe Ala Lys Gly Phe Arg
             290                 295                 300

Asp Thr Gly Asn Gly Arg Arg Glu Lys Arg Gln Gln Leu Thr Leu Gln
305                 310                 315                 320

Ser Met Arg Val Phe Asp Glu Arg His Lys Lys Glu Asn Gly Thr Ser
                 325                 330                 335

Asp Glu Ser Ser Ser Glu Gln Ala Ala Phe Asn Cys Phe Ala Gln Ala
             340                 345                 350

Ser Ser Pro Ala Ala Ser Thr Val Gly Thr Ser Asn Leu Lys Asp Leu
             355                 360                 365

Cys Pro Ser Glu Gly Glu Ser Asp Ala Glu Ala Glu Ser Lys Glu Glu
             370                 375                 380

His Gly Pro Glu Ala Cys Asp Ala Ala Lys Ile Ser Thr Thr Thr Ser
385                 390                 395                 400

Glu Glu Pro Cys Arg Asp Lys Gly Ser Pro Ala Val Lys Ala His Leu
                 405                 410                 415

Phe Ala Ala Glu Arg Pro Arg Asp Ser Gly Arg Leu Asp Lys Ala Ser
             420                 425                 430

Pro Asp Ser Arg His Ser Pro Ala Thr Ile Ser Ser Ser Thr Arg Gly
```

-continued

```
              435                 440                 445
Leu Gly Ala Glu Glu Arg Arg Ser Pro Val Arg Glu Gly Thr Ala Pro
        450                 455                 460

Ala Lys Val Glu Glu Ala Arg Ala Leu Pro Gly Lys Glu Ala Phe Ala
465                 470                 475                 480

Pro Leu Thr Val Gln Thr Asp Ala Ala Arg Ser Ser Val His Arg His
                485                 490                 495

Pro Phe Arg Asn Leu Asn Thr Met Arg Pro Arg Leu Arg Tyr Ser Pro
            500                 505                 510

Tyr Ser Ile Pro Val Pro Val Pro Asp Gly Ser Ser Leu Leu Thr Thr
        515                 520                 525

Ala Leu Ala Ala Ser Pro Ala Ser Val Ala Val Asp Ser Gly Ser Glu
        530                 535                 540

Leu Asn Ser Arg Ser Ser Thr Leu Ser Ser Ser Ser Met Ser Leu Ser
545                 550                 555                 560

Pro Lys Leu Cys Ala Glu Lys Glu Ala Ala Thr Ser Glu Leu Gln Ser
                565                 570                 575

Ile Gln Arg Leu Val Ser Gly Leu Glu Ala Lys Pro Asp Arg Ser Arg
            580                 585                 590

Ser Ala Ser Pro
            595
```

TBX3 GENE AND METHODS OF USING IT

DESCRIPTION OF THE DRAWINGS

SEQ ID NOS 1 and 2 show the nucleotide and amino acid sequences of Tbx3-pr408. The polynucleotides are human cDNAs.

FIG. 1 shows the amino acid comparisons between Tbx3-pr408 (SEQ ID NO 2), NM_005996 (SEQ ID NO 3), XM_016321 (SEQ ID NO 4), and NM_016569 (SEQ ID NO 5).

DESCRIPTION OF THE INVENTION

The present invention relates to all facets of Tbx3-pr408, polypeptides encoded by it, antibodies and specific binding partners thereto, and their applications to research, diagnosis, drug discovery, therapy, clinical medicine, forensic science and medicine, etc. Tbx3-pr408 polynucleotides, polypeptides, antibodies, etc., are useful in variety of ways, including, but not limited to, as a molecular markers, as drug targets, and for detecting, diagnosing, staging, monitoring, prognosticating, preventing or treating, determining predisposition to, etc., diseases and conditions, such as mammary-ulnar syndrome and other developmental disorders associated with it, as well as conditions associated with the adult tissues in which Tbx3-pr408 is expressed. The present invention also relates to methods of using the polynucleotides and related products (proteins, antibodies, etc.) in business and computer-related methods, e.g., advertising, displaying, offering, selling, etc., such products for sale, commercial use, licensing, etc.

Tbx3-pr408 codes for a polypeptide having 723 amino acids. It is a transcription factor. The nucleotide and amino acid sequences of Tbx3-pr408 are shown in SEQ ID NOS 1 and 2. A T box domain, having DNA-binding activity, is located at about amino acid positions 102–290.

Figure 1A:
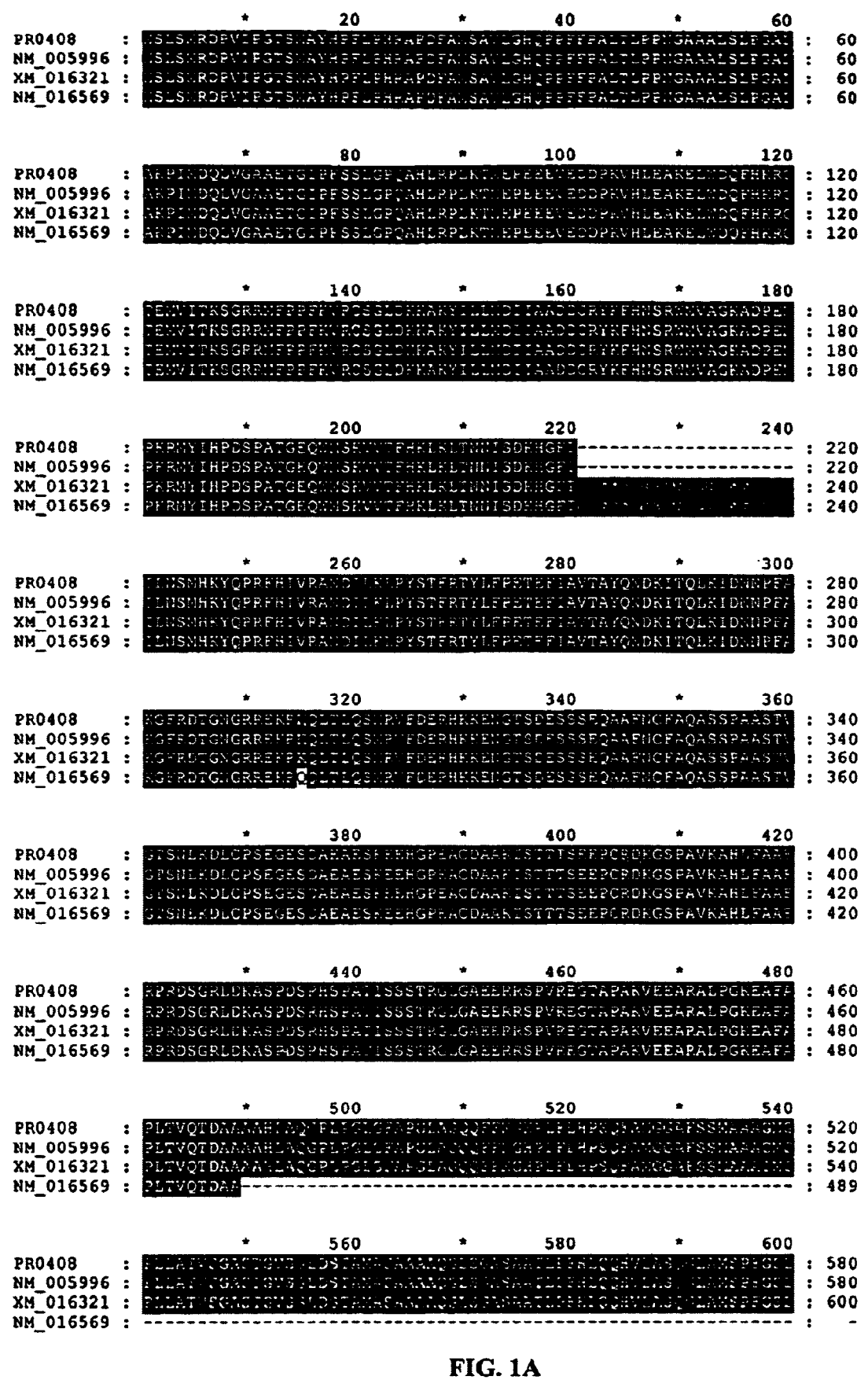

Tbx3-pr408 is a transcript of the Tbx3 gene. See, e.g., He et al., *Proc. Natl. Acad. Sci.*, 96:10212–10217, 1999. It maps to chromosomal position 12q24.1. Mutations in this gene cause ulnar-mammary syndrome, a disease associated with anomalies in limb, apocrine and genital development. Bamshad et al., *Nat. Genet.*, 16:311–316, 1997. FIG. 1 shows the alignment between Tbx3-pr408 and previously known transcripts (NM_005996, XM_016321, and NM_016569) of the Tbx3 gene. As indicated in FIG. 1, Pr408 is decidedly different. In addition to other differences, XM_016321, and NM_016569 contain a 20 amino acid insertion in the T box domain between amino acids 220 and 221 of Tbx3-pr408. This insertion appears to alter the DNA-binding activity of the T box. NM_005996 is at least one amino acid shorter than Tbx3-pr408 and contains different sequence at amino acid positions 596–608.

Tbx3-pr408 has several different biological activities, including, e.g., transcription modulatory activity, and DNA-binding activity. Its activity can be determined routinely. For instance, its transcriptional regulatory activity can be assessed in transcription reporter assays in which Tbx3-pr408, or fragments thereof, can be fused DNA-binding elements (e.g., LexA or Gal4) and/or transactivators, that are used to modulate expression of reporter genes, e.g., as described in He et al., *Proc. Natl. Acad. Sci.*, 96:10212–10217, 1999. By the phrase "transcription regulatory activity," it is meant that the polypeptide modulates transcription of a gene. This modulatory activity can be activation or repression (e.g., He et al. describe repression for a Tbx3 domain). DNA-binding activity can be determined using gel-shift assays.

Consistent with the phenotype of mammary-ulnar syndrome, Tbx3-pr408 is expressed in the testes and prostate. Additionally, it is expressed at high levels in the adrenal gland, heart, lung, and muscle. Lower levels are observed in other tissues, as well. Tissues were also assayed for the presence of the Tbx3 transcript having the insertion between amino acids 220 and 221. Both this transcript and Tbx3-pr408 were expressed in most tissues, however, Tbx3-pr408 was more abundant. Heart expression is particularly striking since mutations in the Tbx5 gene, adjacent to the Tbx3 gene on chromosome 12, is associated with cardiac anomalies, suggesting that both genes may play a role in heart development.

In addition to its association with ulnar-mammary syndrome, Tbx3-pr408 may also have a role in other developmental disorders, including, e.g., spinal muscular atrophy (congenital nonprogressive, of lower limbs), type C brachydactyly, B-cell non-Hodgkin lymphoma, and scapuloperoneal spinal muscular atrophy (New England type). Nucleic acids of the present invention can be used as linkage markers, diagnostic targets, therapeutic targets, for any of the mentioned disorders, as well as any disorders or genes mapping in proximity to it.

Nucleic Acids

A mammalian polynucleotide, or fragment thereof, of the present invention is a polynucleotide having a nucleotide sequence obtainable from a natural source. It therefore includes naturally-occurring normal, naturally-occurring mutant, and naturally-occurring polymorphic alleles (e.g., SNPs), differentially-spliced transcripts, splice-variants, etc. By the term "naturally-occurring," it is meant that the polynucleotide is obtainable from a natural source, e.g., animal tissue and cells, body fluids, tissue culture cells, forensic samples. Natural sources include, e.g., living cells obtained from tissues and whole organisms, tumors, cultured cell lines, including primary and immortalized cell lines. Naturally-occurring mutations can include deletions (e.g., a truncated amino- or carboxy-terminus), substitutions, inversions, or additions of nucleotide sequence. These genes can be detected and isolated by polynucleotide hybridization according to methods which one skilled in the art would know, e.g., as discussed below.

A polynucleotide according to the present invention can be obtained from a variety of different sources. It can be obtained from DNA or RNA, such as polyadenylated mRNA or total RNA, e.g., isolated from tissues, cells, or whole organism. The polynucleotide can be obtained directly from DNA or RNA, from a cDNA library, from a genomic library, etc. The polynucleotide can be obtained from a cell or tissue (e.g., from an embryonic or adult tissues) at a particular stage of development, having a desired genotype, phenotype, disease status, etc. These sequences can be obtained by any suitable method, e.g., using a partial sequence as a probe to select a full-length cDNA from a library containing full-length inserts. A polynucleotide which "codes without interruption" refers to a polynucleotide having a continuous open reading frame ("ORF") as compared to an ORF which is interrupted by introns or other noncoding sequences.

Polynucleotides and polypeptides (including any part of Tbx3-pr408) can be excluded as compositions from the present invention if, e.g., listed in a publicly available databases on the day this application was filed and/or disclosed in a patent application having an earlier filing or priority date than this application and/or conceived and/or reduced to practice earlier than a polynucleotide in this application.

As described herein, the phrase "an isolated polynucleotide which is SEQ ID NO," or "an isolated polynucleotide which is selected from SEQ ID NO," refers to an isolated nucleic acid molecule from which the recited sequence was derived (e.g., a cDNA derived from mRNA; cDNA derived from genomic DNA). Because of sequencing errors, typographical errors, etc., the actual naturally-occurring sequence may differ from a SEQ ID listed herein. Thus, the phrase indicates the specific molecule from which the sequence was derived, rather than a molecule having that exact recited nucleotide sequence, analogously to how a culture depository number refers to a specific cloned fragment in a cryotube.

As explained in more detail below, a polynucleotide sequence of the invention can contain the complete sequence as shown in SEQ ID NO 1, degenerate sequences thereof, anti-sense, muteins thereof, genes comprising said sequences, full-length cDNAs comprising said sequences, complete genomic sequences, fragments thereof, homologs, primers, nucleic acid molecules which hybridize thereto, derivatives thereof, etc.

Constructs

A polynucleotide of the present invention can comprise additional polynucleotide sequences, e.g., sequences to enhance expression, detection, uptake, cataloging, tagging, etc. A polynucleotide can include only coding sequence; a coding sequence and additional non-naturally occurring or heterologous coding sequence (e.g., sequences coding for leader, signal, secretory, targeting, enzymatic, fluorescent, antibiotic resistance, and other functional or diagnostic peptides); coding sequences and non-coding sequences, e.g., untranslated sequences at either a 5' or 3' end, or dispersed in the coding sequence, e.g., introns.

A polynucleotide according to the present invention also can comprise an expression control sequence operably linked to a polynucleotide as described above. The phrase "expression control sequence" means a polynucleotide sequence that regulates expression of a polypeptide coded for by a polynucleotide to which it is functionally ("operably") linked. Expression can be regulated at the level of the mRNA or polypeptide. Thus, the expression control sequence includes mRNA-related elements and protein-related elements. Such elements include promoters, enhancers (viral or cellular), ribosome binding sequences, transcriptional terminators, etc. An expression control sequence is operably linked to a nucleotide coding sequence when the expression control sequence is positioned in such a manner to effect or achieve expression of the coding sequence. For example, when a promoter is operably linked 5' to a coding sequence, expression of the coding sequence is driven by the promoter. Expression control sequences can include an initiation codon and additional nucleotides to place a partial nucleotide sequence of the present invention in-frame in order to produce a polypeptide (e.g., pET vectors from Promega have been designed to permit a molecule to be inserted into all three reading frames to identify the one that results in polypeptide expression). Expression control sequences can be heterologous or endogenous to the normal gene.

A polynucleotide of the present invention can also comprise nucleic acid vector sequences, e.g., for cloning, expression, amplification, selection, etc. Any effective vector can be used. A vector is, e.g., a polynucleotide molecule which can replicate autonomously in a host cell, e.g., containing an origin of replication. Vectors can be useful to perform manipulations, to propagate, and/or obtain large quantities of the recombinant molecule in a desired host. A skilled worker can select a vector depending on the purpose desired, e.g., to propagate the recombinant molecule in bacteria, yeast, insect, or mammalian cells. The following vectors are provided by way of example. Bacterial: pQE70, pQE60, pQE-9 (Qiagen), pBS, pD10, Phagescript, phiX174, pBK Phagemid, pNH8A, pNH16a, pNH18Z, pNH46A (Stratagene); Bluescript KS+II (Stratagene); ptrc99a, pKK223-3, pKK233-3, pDR54 0, pRIT5 (Pharmacia). Eukaryotic: PWLNEO, pSV2CAT, pOG44, pXT1, pSG (Stratagene), pSVK3, PBPV, PMSG, pSVL (Pharmacia), pCR2.1/TOPO, pCRII/TOPO, pCR4/TOPO, pTrcHisB, pCMV6-XL4, etc. However, any other vector, e.g., plasmids, viruses, or parts thereof, may be used as long as they are replicable and viable in the desired host. The vector can also comprise sequences which enable it to replicate in the host whose genome is to be modified.

Hybridization

Polynucleotide hybridization, as discussed in more detail below, is useful in a variety of applications, including, in gene detection methods, for identifying mutations, for making mutations, to identify homologs in the same and different species, to identify related members of the same gene family, in diagnostic and prognostic assays, in therapeutic applications (e.g., where an antisense polynucleotide is used to inhibit expression), etc.

The ability of two single-stranded polynucleotide preparations to hybridize together is a measure of their nucleotide sequence complementarity, e.g., base-pairing between nucleotides, such as A-T, G-C, etc. The invention thus also relates to polynucleotides, and their complements, which hybridize to a polynucleotide comprising a nucleotide sequence as set forth in SEQ ID NO 1 and genomic sequences thereof. A nucleotide sequence hybridizing to the latter sequence will have a complementary polynucleotide strand, or act as a template for one in the presence of a polymerase (i.e., an appropriate polynucleotide synthesizing enzyme). The present invention includes both strands of polynucleotide, e.g., a sense strand and an anti-sense strand.

Hybridization conditions can be chosen to select polynucleotides which have a desired amount of nucleotide complementarity with the nucleotide sequences set forth in SEQ ID NO 1 and genomic sequences thereof. A polynucleotide capable of hybridizing to such sequence, preferably, possesses, e.g., about 70%, 75%, 80%, 85%, 87%, 90%, 92%, 95%, 97%, 99%, or 100% complementarity, between the sequences. The present invention particularly relates to polynucleotide sequences which hybridize to the nucleotide sequences set forth in SEQ ID NO 1 or genomic sequences thereof, under low or high stringency conditions. These conditions can be used, e.g., to select corresponding homologs in non-human species.

Polynucleotides which hybridize to polynucleotides of the present invention can be selected in various ways. Filter-type blots (i.e., matrices containing polynucleotide, such as nitrocellulose), glass chips, and other matrices and substrates comprising polynucleotides (short or long) of interest, can be incubated in a prehybridization solution (e.g., 6×SSC, 0.5% SDS, 100 µg/ml denatured salmon sperm DNA, 5× Denhardt's solution, and 50% formamide), at 22–68° C., overnight, and then hybridized with a detectable polynucleotide probe under conditions appropriate to achieve the desired stringency. In general, when high homology or sequence identity is desired, a high temperature can be used (e.g., 65° C.). As the homology drops, lower washing temperatures are used. For salt concentrations, the lower the salt concentration, the higher the stringency. The length of the probe is another consideration. Very short probes (e.g., less than 100 base pairs) are washed at lower temperatures, even if the homology is high. With short probes, formamide can be omitted. See, e.g., *Current Protocols in Molecular Biology*, Chapter 6, Screening of Recombinant Libraries; Sambrook et al., *Molecular Cloning*, 1989, Chapter 9.

For instance, high stringency conditions can be achieved by incubating the blot overnight (e.g., at least 12 hours) with a long polynucleotide probe in a hybridization solution containing, e.g., about 5×SSC, 0.5% SDS, 100 µg/ml denatured salmon sperm DNA and 50% formamide, at 42° C. Blots can be washed at high stringency conditions that allow, e.g., for less than 5% bp mismatch (e.g., wash twice in 0.1% SSC and 0.1% SDS for 30 min at 65° C.), i.e., selecting sequences having 95% or greater sequence identity.

Other non-limiting examples of high stringency conditions includes a final wash at 65° C. in aqueous buffer containing 30 mM NaCl and 0.5% SDS. Another example of high stringent conditions is hybridization in 7% SDS, 0.5 M $NaPO_4$, pH 7, 1 mM EDTA at 50° C., e.g., overnight, followed by one or more washes with a 1% SDS solution at 42° C. Whereas high stringency washes can allow for less than 5% mismatch, reduced or low stringency conditions can permit up to 20% nucleotide mismatch. Hybridization at low stringency can be accomplished as above, but using lower formamide conditions, lower temperatures and/or lower salt concentrations, as well as longer periods of incubation time.

Hybridization can also be based on a calculation of melting temperature (Tm) of the hybrid formed between the probe and its target, as described in Sambrook et al. Generally, the temperature Tm at which a short oligonucleotide (containing 18 nucleotides or fewer) will melt from its target sequence is given by the following equation: Tm= (number of A's and T's)×2° C.+(number of C's and G's)×4° C. For longer molecules, Tm=81.5+16.6 $\log_{10}[Na^+]$+0.41 (%GC)−600/N where $[Na^+]$ is the molar concentration of sodium ions, %GC is the percentage of GC base pairs in the probe, and N is the length. Hybridization can be carried out at several degrees below this temperature to ensure that the probe and target can hybridize. Mismatches can be allowed for by lowering the temperature even further.

Stringent conditions can be selected to isolate sequences, and their complements, which have, e.g., at least about 90%, 95%, or 97%, nucleotide complementarity between the probe (e.g., a short polynucleotide of SEQ ID NO 1 or genomic sequences thereof) and a target polynucleotide.

Other homologs of polynucleotides of the present invention can be obtained from mammalian and non-mammalian sources according to various methods. For example, hybridization with a polynucleotide can be employed to select homologs, e.g., as described in Sambrook et al., *Molecular Cloning*, Chapter 11, 1989. Such homologs can have varying amounts of nucleotide and amino acid sequence identity and similarity to such polynucleotides of the present invention. Mammalian organisms include, e.g., mice, rats, monkeys, pigs, cows, etc. Non-mammalian organisms include, e.g., vertebrates, invertebrates, zebra fish, chicken, Drosophila, C. elegans, Xenopus, yeast such as *S. pombe, S. cerevisiae*, roundworms, prokaryotes, plants, Arabidopsis, artemia, viruses, etc. The degree of nucleotide sequence identity between human and mouse can be about, e.g. 70% or more, 85% or more for open reading frames, etc.

Alignment

Alignments can be accomplished by using any effective algorithm. For pairwise alignments of DNA sequences, the methods described by Wilbur-Lipman (e.g., Wilbur and Lipman, *Proc. Natl. Acad. Sci.*, 80:726–730, 1983) or Martinez/Needleman-Wunsch (e.g., Martinez, *Nucleic Acid Res.*, 11:4629–4634, 1983) can be used. For instance, if the Martinez/Needleman-Wunsch DNA alignment is applied, the minimum match can be set at 9, gap penalty at 1.10, and gap length penalty at 0.33. The results can be calculated as a similarity index, equal to the sum of the matching residues divided by the sum of all residues and gap characters, and then multiplied by 100 to express as a percent. Similarity index for related genes at the nucleotide level in accordance with the present invention can be greater than 70%, 80%, 85%, 90%, 95%, 99%, or more. Pairs of protein sequences can be aligned by the Lipman-Pearson method (e.g., Lipman and Pearson, *Science*, 227:1435–1441, 1985) with k-tuple set at 2, gap penalty set at 4, and gap length penalty set at 12. Results can be expressed as percent similarity index, where related genes at the amino acid level in accordance with the present invention can be greater than 65%, 70%, 75%, 80%, 85%, 90%, 95%, 99%, or more. Various commercial and free sources of alignment programs are available, e.g., MegAlign by DNA Star, BLAST (National Center for Biotechnology Information), BCM (Baylor College of Medicine) Launcher, etc.

Percent sequence identity can also be determined by other conventional methods, e.g., as described in Altschul et al., *Bull. Math. Bio.* 48: 603–616, 1986 and Henikoff and Henikoff, *Proc. Natl. Acad. Sci. USA* 89:10915–10919, 1992.

Specific Polynucleotide Probes

A polynucleotide of the present invention can comprise any continuous nucleotide sequence of SEQ ID NO 1, sequences which share sequence identity thereto, or complements thereof. The term "probe" refers to any substance that can be used to detect, identify, isolate, etc., another substance. A polynucleotide probe is comprised of nucleic acid can be used to detect, identify, etc., other nucleic acids, such as DNA and RNA. Useful probes, include, e.g., probes on either side of amino acid positions 220–221 (i.e., where NM_005996 and XM_016321 have insertions), e.g., a probe selected from nucleotide positions 1112–1183 and from nucleotide positions 1184–1255) to determine whether the insertion is present or not.

These polynucleotides can be of any desired size that is effective to achieve the specificity desired. For example, a probe can be from about 7 or 8 nucleotides to several thousand nucleotides, depending upon its use and purpose. For instance, a probe used as a primer PCR can be shorter than a probe used in an ordered array of polynucleotide probes. Probe sizes vary, and the invention is not limited in any way by their size, e.g., probes can be from about 7–2000 nucleotides, 7–1000, 8–700, 8–600, 8–500, 8–400, 8–300, 8–150, 8–100, 8–75, 7–50, 10–25, 14–16, at least about 8, at least about 10, at least about 15, at least about 25, etc. The polynucleotides can have non-naturally-occurring nucleotides, e.g., inosine, AZT, 3TC, etc. The polynucleotides can have 100% sequence identity or complementarity to a sequence of SEQ ID NO 1, or it can have mismatches or nucleotide substitutions, e.g., 1, 2, 3, 4, or 5 substitutions. The probes can be single-stranded or double-stranded.

In accordance with the present invention, a polynucleotide can be present in a kit, where the kit includes, e.g., one or more polynucleotides, a desired buffer (e.g., phosphate, tris, etc.), detection compositions, RNA or cDNA from different tissues to be used as controls, libraries, etc. The polynucleotide can be labeled or unlabeled, with radioactive or non-radioactive labels as known in the art. Kits can comprise one or more pairs of polynucleotides for amplifying nucleic acids specific for Tbx3-pr408, e.g., comprising a forward and reverse primer effective in PCR. These include both sense and anti-sense orientations. For instance, in PCR-based methods (such as RT-PCR), a pair of primers are typically used, one having a sense sequence and the other having an antisense sequence.

Another aspect of the present invention is a nucleotide sequence that is specific to, or for, a selective polynucleotide. The phrases "specific for" or "specific to" a polynucleotide have a functional meaning that the polynucleotide can be used to identify the presence of one or more target genes in a sample. It is specific in the sense that it can be used to detect polynucleotides above background noise ("non-specific binding"). A specific sequence is a defined order of nucleotides which occurs in the polynucleotide, e.g., in the nucleotide sequences of SEQ ID NO 1. A probe or mixture of probes can comprise a sequence or sequences that are specific to a plurality of target sequences, e.g., where the sequence is a consensus sequence, a functional domain, etc., e.g., capable of recognizing a family of related genes. Such sequences can be used as probes in any of the methods described herein or incorporated by reference. Both sense and antisense nucleotide sequences are included. A specific polynucleotide according to the present invention can be determined routinely.

A polynucleotide comprising a specific sequence can be used as a hybridization probe to identify the presence of, e.g., human or mouse polynucleotide, in a sample comprising a mixture of polynucleotides, e.g., on a Northern blot. Hybridization can be performed under high stringent conditions (see, above) to select polynucleotides (and their complements which can contain the coding sequence) having at least 90%, 95%, 99%, etc., identity (i.e., complementarity) to the probe, but less stringent conditions can also be used. A specific polynucleotide sequence can also be fused in-frame, at either its 5' or 3' end, to various nucleotide sequences as mentioned throughout the patent, including coding sequences for enzymes, detectable markers, GFP, etc, expression control sequences, etc.

A polynucleotide probe, especially one that is specific to a polynucleotide of the present invention, can be used in gene detection and hybridization methods as already described. In one embodiment, a specific polynucleotide probe can be used to detect whether a particular tissue or cell-type is present in a target sample. To carry out such a method, a selective polynucleotide can be chosen which is characteristic of the desired target tissue. Such polynucleotide is preferably chosen so that it is expressed or displayed in the target tissue, but not in other tissues which are present in the sample. For instance, if detection of prostate is desired, it may not matter whether the selective polynucleotide is expressed in other tissues, as long as it is not expressed in cells normally present in blood, e.g., peripheral blood mononuclear cells. Starting from the selective polynucleotide, a specific polynucleotide probe can be designed which hybridizes (if hybridization is the basis of the assay) under the hybridization conditions to the selective polynucleotide, whereby the presence of the selective polynucleotide can be determined.

Probes which are specific for polynucleotides of the present invention can also be prepared using involve transcription-based systems, e.g., incorporating an RNA polymerase promoter into a selective polynucleotide of the present invention, and then transcribing anti-sense RNA using the polynucleotide as a template. See, e.g., U.S. Pat. No. 5,545,522.

Polynucleotide Composition

A polynucleotide according to the present invention can comprise, e.g., DNA, RNA, synthetic polynucleotide, peptide polynucleotide, modified nucleotides, dsDNA, ssDNA, ssRNA, dsRNA, and mixtures thereof A polynucleotide can be single- or double-stranded, triplex, DNA:RNA, duplexes, comprise hairpins, and other secondary structures, etc. Nucleotides comprising a polynucleotide can be joined via various known linkages, e.g., ester, sulfamate, sulfamide, phosphorothioate, phosphoramidate, methylphosphonate, carbamate, etc., depending on the desired purpose, e.g., resistance to nucleases, such as RNAse H, improved in vivo stability, etc. See, e.g., U.S. Pat. No. 5,378,825. Any desired nucleotide or nucleotide analog can be incorporated, e.g., 6-mercaptoguanine, 8-oxo-guanine, etc.

Various modifications can be made to the polynucleotides, such as attaching detectable markers (avidin, biotin, radioactive elements, fluorescent tags and dyes, energy transfer labels, energy-emitting labels, binding partners, etc.) or moieties which improve hybridization, detection, and/or stability. The polynucleotides can also be attached to solid supports, e.g., nitrocellulose, magnetic or paramagnetic microspheres (e.g., as described in U.S. Pat. No. 5,411,863; U.S. Pat. No. 5,543,289; for instance, comprising ferromagnetic, supermagnetic, paramagnetic, superparamagnetic, iron oxide and polysaccharide), nylon, agarose, diazotized cellulose, latex solid microspheres, polyacrylamides, etc., according to a desired method. See, e.g., U.S. Pat. Nos. 5,470,967, 5,476,925, and 5,478,893.

Polynucleotide according to the present invention can be labeled according to any desired method. The polynucleotide can be labeled using radioactive tracers such as $^{32}P$, $^{35}S$, $^{3}H$, or $^{14}C$, to mention some commonly used tracers. The radioactive labeling can be carried out according to any method, such as, for example, terminal labeling at the 3' or 5' end using a radiolabeled nucleotide, polynucleotide kinase (with or without dephosphorylation with a phosphatase) or a ligase (depending on the end to be labeled). A non-radioactive labeling can also be used, combining a polynucleotide of the present invention with residues having immunological properties (antigens, haptens), a specific affinity for certain reagents (ligands), properties enabling detectable enzyme reactions to be completed (enzymes or coenzymes, enzyme substrates, or other substances involved in an enzymatic reaction), or characteristic physical properties, such as fluorescence or the emission or absorption of light at a desired wavelength, etc.

Nucleic Acid Detection Methods

Another aspect of the present invention relates to methods and processes for detecting Tbx3-pr408. Detection methods have a variety of applications, including for diagnostic, prognostic, forensic, and research applications. To accomplish gene detection, a polynucleotide in accordance with the present invention can be used as a "probe." The term "probe" or "polynucleotide probe" has its customary meaning in the art, e.g., a polynucleotide which is effective to identify (e.g., by hybridization), when used in an appropriate process, the presence of a target polynucleotide to which it is designed. Identification can involve simply determining presence or absence, or it can be quantitative, e.g., in assessing amounts of a gene or gene transcript present in a sample. Probes can be useful in a variety of ways, such as for diagnostic purposes, to identify homologs, and to detect, quantitate, or isolate a polynucleotide of the present invention in a test sample.

Assays can be utilized which permit quantification and/or presence/absence detection of a target nucleic acid in a sample. Assays can be performed at the single-cell level, or in a sample comprising many cells, where the assay is "averaging" expression over the entire collection of cells and tissue present in the sample. Any suitable assay format can be used, including, but not limited to, e.g., Southern blot analysis, Northern blot analysis, polymerase chain reaction ("PCR") (e.g., Saiki et al., *Science*, 241:53, 1988; U.S. Pat. Nos. 4,683,195, 4,683,202, and 6,040,166; PCR *Protocols: A Guide to Methods and Applications*, Innis et al., eds., Academic Press, New York, 1990), reverse transcriptase polymerase chain reaction ("RT-PCR"), anchored PCR, rapid amplification of cDNA ends ("RACE") (e.g., Schaefer in *Gene Cloning and Analysis: Current Innovations*, Pages 99–115, 1997), ligase chain reaction ("LCR") (EP 320 308), one-sided PCR (Ohara et al., *Proc. Natl. Acad. Sci.*, 86:5673–5677, 1989), indexing methods (e.g., U.S. Pat. No. 5,508,169), in situ hybridization, differential display (e.g., Liang et al., *Nucl. Acid. Res.*, 21:3269–3275, 1993; U.S. Pat. Nos. 5,262,311, 5,599,672 and 5,965,409; WO97/18454; Prashar and Weissman, *Proc. Natl. Acad. Sci.*, 93:659–663, and U.S. Pat. Nos. 6,010,850 and 5,712,126; Welsh et al., *Nucleic Acid Res.*, 20:4965–4970, 1992, and U.S. Pat. No. 5,487,985) and other RNA fingerprinting techniques, nucleic acid sequence based amplification ("NASBA") and other transcription based amplification systems (e.g., U.S. Pat. Nos. 5,409,818 and 5,554,527; WO88/10315), polynucleotide arrays (e.g., U.S. Pat. Nos. 5,143,854, 5,424,186; 5,700,637, 5,874,219, and 6,054,270; PCT WO92/10092; PCT WO90/15070), Qbeta Replicase (PCT/US87/00880), Strand Displacement Amplification ("SDA"), Repair Chain Reaction ("RCR"), nuclease protection assays, subtraction-based methods, Rapid-Scan™, etc. Additional useful methods include, but are not limited to, e.g., template-based amplification methods, competitive PCR (e.g., U.S. Pat. No. 5,747,251), redox-based assays (e.g., U.S. Pat. No. 5,871, 918), Taqman-based assays (e.g., Holland et al., *Proc. Natl. Acad, Sci.*, 88:7276–7280, 1991; U.S. Pat. Nos. 5,210,015 and 5,994,063), real-time fluorescence-based monitoring (e.g., U.S. Pat. No. 5,928,907), molecular energy transfer labels (e.g., U.S. Pat. Nos. 5,348,853, 5,532,129, 5,565,322, 6,030,787, and 6,117,635; Tyagi and Kramer, *Nature Biotech.*, 14:303–309, 1996). Any method suitable for single cell analysis of gene or protein expression can be used, including in situ hybridization, immunocytochemistry, MACS, FACS, flow cytometry, etc. For single cell assays, expression products can be measured using antibodies, PCR, or other types of nucleic acid amplification (e.g., Brady et al., *Methods Mol. & Cell. Biol.* 2, 17–25, 1990; Eberwine et al., 1992, *Proc. Natl. Acad. Sci.*, 89, 3010–3014, 1992; U.S. Pat. No. 5,723,290). These and other methods can be carried out conventionally, e.g., as described in the mentioned publications.

Many of such methods may require that the polynucleotide is labeled, or comprises a particular nucleotide type useful for detection. The present invention includes such modified polynucleotides that are necessary to carry out such methods. Thus, polynucleotides can be DNA, RNA, DNA:RNA hybrids, PNA, etc., and can comprise any modification or substituent which is effective to achieve detection.

Detection can be desirable for a variety of different purposes, including research, diagnostic, prognostic, and forensic. For diagnostic purposes, it may be desirable to identify the presence or quantity of a polynucleotide sequence in a sample, where the sample is obtained from tissue, cells, body fluids, etc. In a preferred method as described in more detail below, the present invention relates to a method of detecting a polynucleotide comprising, contacting a target polynucleotide in a test sample with a polynucleotide probe under conditions effective to achieve hybridization between the target and probe; and detecting hybridization.

Any test sample in which it is desired to identify a polynucleotide or polypeptide thereof can be used, including, e.g., blood, urine, saliva, stool (for extracting nucleic acid, see, e.g., U.S. Pat. No. 6,177,251), swabs comprising tissue, biopsied tissue, tissue sections, cultured cells, etc.

Detection can be accomplished in combination with polynucleotide probes for other genes, e.g., genes which are expressed in other disease states, tissues, cells, such as brain, heart, kidney, spleen, thymus, liver, stomach, small intestine, colon, muscle, lung, testis, placenta, pituitary, thyroid, skin, adrenal gland, pancreas, salivary gland, uterus, ovary, prostate gland, peripheral blood cells (T-cells, lymphocytes, etc.), embryo, normal breast fat, adult and embryonic stem cells, specific cell-types, such as endothelial, epithelial, myocytes, adipose, luminal epithelial, basoepithelial, myoepithelial, stromal cells, etc.

Polynucleotides can be used in wide range of methods and compositions, including for detecting, diagnosing, staging, grading, assessing, prognosticating, etc. diseases and disorders associated with Tbx3-pr408, for monitoring or assessing therapeutic and/or preventative measures, in ordered arrays, etc. Any method of detecting genes and polynucleotides of SEQ ID NO 1 can be used; certainly, the present invention is not to be limited how such methods are implemented.

Along these lines, the present invention relates to methods of detecting Tbx3-pr408 in a sample comprising nucleic acid. Such methods can comprise one or more the following steps in any effective order, e.g., contacting said sample with a polynucleotide probe under conditions effective for said probe to hybridize specifically to nucleic acid in said sample, and detecting the presence or absence of probe hybridized to nucleic acid in said sample, wherein said probe is a polynucleotide which is SEQ ID NO 1, a polynucleotide having, e.g., about 70%, 80%, 85%, 90%, 95%, 99%, or more sequence identity thereto, effective or specific fragments thereof, or complements thereto. The detection method can be applied to any sample, e.g., cultured primary, secondary, or established cell lines, tissue biopsy, blood, urine, stool, cerebral spinal fluid, and other bodily fluids, for any purpose.

Contacting the sample with probe can be carried out by any effective means in any effective environment. It can be accomplished in a solid, liquid, frozen, gaseous, amorphous, solidified, coagulated, colloid, etc., mixtures thereof, matrix. For instance, a probe in an aqueous medium can be contacted with a sample which is also in an aqueous medium, or which is affixed to a solid matrix, or vice-versa.

Generally, as used throughout the specification, the term "effective conditions" means, e.g., the particular milieu in which the desired effect is achieved. Such a milieu, includes, e.g., appropriate buffers, oxidizing agents, reducing agents, pH, co-factors, temperature, ion concentrations, suitable age and/or stage of cell (such as, in particular part of the cell cycle, or at a particular stage where particular genes are being expressed) where cells are being used, culture conditions (including substrate, oxygen, carbon dioxide, etc.). When hybridization is the chosen means of achieving detection, the probe and sample can be combined such that the resulting conditions are functional for said probe to hybridize specifically to nucleic acid in said sample.

The phrase "hybridize specifically" indicates that the hybridization between single-stranded polynucleotides is based on nucleotide sequence complementarity. The effective conditions are selected such that the probe hybridizes to a preselected and/or definite target nucleic acid in the sample. For instance, if detection of a polynucleotide set forth in SEQ ID NO 1 is desired, a probe can be selected which can hybridize to such target gene under high stringent conditions, without significant hybridization to other genes in the sample. To detect homologs of a polynucleotide set forth in SEQ ID NO 1, the effective hybridization conditions can be less stringent, and/or the probe can comprise codon degeneracy, such that a homolog is detected in the sample.

As already mentioned, the methods can be carried out by any effective process, e.g., by Northern blot analysis, polymerase chain reaction (PCR), reverse transcriptase PCR, RACE PCR, in situ hybridization, etc., as indicated above. When PCR based techniques are used, two or more probes are generally used. One probe can be specific for a defined sequence which is characteristic of a selective polynucleotide, but the other probe can be specific for the selective polynucleotide, or specific for a more general sequence, e.g., a sequence such as polyA which is characteristic of mRNA, a sequence which is specific for a promoter, ribosome binding site, or other transcriptional features, a consensus sequence (e.g., representing a functional domain). For the former aspects, 5' and 3' probes (e.g., polyA, Kozak, etc.) are preferred which are capable of specifically hybridizing to the ends of transcripts. When PCR is utilized, the probes can also be referred to as "primers" in that they can prime a DNA polymerase reaction.

In addition to testing for the presence or absence of polynucleotides, the present invention also relates to determining the amounts at which polynucleotides of the present invention are expressed in sample and determining the differential expression of such polynucleotides in samples. Such methods can involve substantially the same steps as described above for presence/absence detection, e.g., contacting with probe, hybridizing, and detecting hybridized probe, but using more quantitative methods and/or comparisons to standards.

The amount of hybridization between the probe and target can be determined by any suitable methods, e.g., PCR, RT-PCR, RACE PCR, Northern blot, polynucleotide microarrays, Rapid-Scan, etc., and includes both quantitative and qualitative measurements. For further details, see the hybridization methods described above and below. Determining by such hybridization whether the target is differentially expressed (e.g., up-regulated or down-regulated) in the sample can also be accomplished by any effective means. For instance, the target's expression pattern in the sample can be compared to its pattern in a known standard, such as in a normal tissue, or it can be compared to another gene in the same sample. When a second sample is utilized for the comparison, it can be a sample of normal tissue that is known not to contain diseased cells. The comparison can be performed on samples which contain the same amount of RNA (such as polyadenylated RNA or total RNA), or, on RNA extracted from the same amounts of starting tissue. Such a second sample can also be referred to as a control or standard. Hybridization can also be compared to a second target in the same tissue sample. Experiments can be performed that determine a ratio between the target nucleic acid and a second nucleic acid (a standard or control), e.g., in a normal tissue. When the ratio between the target and control are substantially the same in a normal and sample, the sample is determined or diagnosed not to contain cells. However, if the ratio is different between the normal and sample tissues, the sample is determined to contain cancer cells. The approaches can be combined, and one or more second samples, or second targets can be used. Any second target nucleic acid can be used as a comparison, including "housekeeping" genes, such as beta-actin, alcohol dehydrogenase, or any other gene whose expression does not vary depending upon the disease status of the cell.

Methods of Identifying Polymorphisms, Mutations, etc., of Tbx3-pr408

Polynucleotides of the present invention can also be utilized to identify mutant alleles, SNPs, gene rearrangements and modifications, and other polymorphisms of the wild-type gene. Mutant alleles, polymorphisms, SNPs, etc., can be identified and isolated from cancers that are known, or suspected to have, a genetic component. Identification of such genes can be carried out routinely (see, above for more guidance), e.g., using PCR, hybridization techniques, direct sequencing, mismatch reactions (see, e.g., above), RFLP analysis, SSCP (e.g., Orita et al., Proc. Natl. Acad. Sci., 86:2766, 1992), etc., where a polynucleotide having a sequence selected from SEQ ID NO 1 is used as a probe. The selected mutant alleles, SNPs, polymorphisms, etc., can be used diagnostically to determine whether a subject has, or is susceptible to a disorder associated with Tbx3-pr408, as well as to design therapies and predict the outcome of the disorder. Methods involve, e.g., diagnosing a disorder associated with Tbx3-pr408 or determining susceptibility to a disorder, comprising, detecting the presence of a mutation in a gene represented by a polynucleotide selected from SEQ ID NO 1. The detecting can be carried out by any effective method, e.g., obtaining cells from a subject, determining the gene sequence or structure of a target gene (using, e.g., mRNA, cDNA, genomic DNA, etc), comparing the sequence or structure of the target gene to the structure of the normal gene, whereby a difference in sequence or structure indicates a mutation in the gene in the subject. Polynucleotides can also be used to test for mutations, SNPs, polymorphisms, etc., e.g., using mismatch DNA repair technology as described in U.S. Pat. No. 5,683,877; U.S. Pat. No. 5,656,430; Wu et al. Proc. Natl. Acad. Sci., 89:8779–8783, 1992.

The present invention also relates to methods of detecting polymorphisms in Tbx3-pr408, comprising, e.g., comparing the structure of: genomic DNA comprising all or part of Tbx3-pr408, mRNA comprising all or part of Tbx3-pr408, cDNA comprising all or part of Tbx3-pr408, or a polypeptide comprising all or part of Tbx3-pr408, with the structure of Tbx3-pr408 gene. The methods can be carried out on a sample from any source, e.g., cells, tissues, body fluids, blood, urine, stool, hair, egg, sperm, cerebral spinal fluid, etc.

These methods can be implemented in many different ways. For example, "comparing the structure" steps include, but are not limited to, comparing restriction maps, nucleotide sequences, amino acid sequences, RFLPs, Dnase sites, DNA methylation fingerprints (e.g., U.S. Pat. No. 6,214, 556), protein cleavage sites, molecular weights, electrophoretic mobilities, charges, ion mobility, etc., between a standard Tbx3-pr408 and a test Tbx3-pr408. The term "structure" can refer to any physical characteristics or configurations which can be used to distinguish between nucleic acids and polypeptides. The methods and instruments used to accomplish the comparing step depends upon the physical characteristics which are to be compared. Thus, various techniques are contemplated, including, e.g., sequencing machines (both amino acid and polynucleotide), electrophoresis, mass spectrometer (U.S. Pat. Nos. 6,093, 541, 6,002,127), liquid chromatography, HPLC, etc.

To carry out such methods, "all or part" of the gene or polypeptide can be compared. For example, if nucleotide sequencing is utilized, the entire gene can be sequenced, including promoter, introns, and exons, or only parts of it can be sequenced and compared, e.g., exon 1, exon 2, etc.
Mutagenesis Mutated polynucleotide sequences of the present invention are useful for various purposes, e.g., to create mutations of the polypeptides they encode, to identify functional regions of genomic DNA, to produce probes for screening libraries, etc. Mutagenesis can be carried out routinely according to any effective method, e.g., oligonucleotide-directed (Smith, M., *Ann. Rev. Genet.* 19:423–463, 1985), degenerate oligonucleotide-directed (Hill et al., *Method Enzymology*, 155:558–568, 1987), region-specific (Myers et al., *Science*, 229:242–246, 1985; Derbyshire et al., *Gene*, 46:145, 1986; Ner et al., DNA, 7:127, 1988), linker-scanning (McKnight and Kingsbury, *Science*, 217:316–324, 1982), directed using PCR, recursive ensemble mutagenesis (Arkin and Yourvan, *Proc. Natl. Acad. Sci.*, 89:7811–7815, 1992), random mutagenesis (e.g., U.S. Pat. Nos. 5,096,815; 5,198,346; and 5,223,409), site-directed mutagenesis (e.g., Walder et al., *Gene*, 42:133, 1986; Bauer et al., *Gene*, 37:73, 1985; Craik, *Bio Techniques*, January 1985, 12–19; Smith et al., *Genetic Engineering: Principles and Methods*, Plenum Press, 1981), phage display (e.g., Lowman et al., *Biochem*. 30:10832–10837, 1991; Ladner et al., U.S. Pat. No. 5,223,409; Huse, WIPO Publication WO92/06204), etc. Desired sequences can also be produced by the assembly of target sequences using mutually priming oligonucleotides (Uhlmann, *Gene*, 71:29–40, 1988). For directed mutagenesis methods, analysis of the three-dimensional structure of the Tbx3-pr408 polypeptide can be used to guide and facilitate making mutants which effect polypeptide activity. Sites of substrate-enzyme interaction or other biological activities can also be determined by analysis of crystal structure as determined by such techniques as nuclear magnetic resonance, crystallography or photoaffinity labeling. See, for example, de Vos et al., *Science* 255:306–312, 1992; Smith et al., *J. Mol. Biol.* 224:899–904, 1992; Wlodaver et al., *FEBS Lett*. 309:59–64, 1992.

FIG. 1 provides guidance on mutations that can be made in Tbx3-pr408, e.g., changing a non-conserved amino acid, e., at amino acid position 295 and/or 609.

In addition, libraries of Tbx3-pr408 and fragments thereof can be used for screening and selection of Tbx3-pr408 variants. For instance, a library of coding sequences can be generated by treating a double-stranded DNA with a nuclease under conditions where the nicking occurs, e.g., only once per molecule, denaturing the double-stranded DNA, renaturing it to for double-stranded DNA that can include sense/antisense pairs from different nicked products, removing single-stranded portions from reformed duplexes by treatment with S1 nuclease, and ligating the resulting DNAs into an expression vecore. By this method, xpression libraries can be made comprising "mutagenized" Tbx3-pr408. The entire coding sequence or parts thereof can be used.

Polynucleotide Expression, Polypeptides Produced Thereby, and Specific-binding Partners Thereto.

A polynucleotide according to the present invention can be expressed in a variety of different systems, in vitro and in vivo, according to the desired purpose. For example, a polynucleotide can be inserted into an expression vector, introduced into a desired host, and cultured under conditions effective to achieve expression of a polypeptide coded for by the polynucleotide, to search for specific binding partners. Effective conditions include any culture conditions which are suitable for achieving production of the polypeptide by the host cell, including effective temperatures, pH, medium, additives to the media in which the host cell is cultured (e.g., additives which amplify or induce expression such as butyrate, or methotrexate if the coding polynucleotide is adjacent to a dhfr gene), cycloheximide, cell densities, culture dishes, etc. A polynucleotide can be introduced into the cell by any effective method including, e.g., naked DNA, calcium phosphate precipitation, electroporation, injection, DEAE-Dextran mediated transfection, fusion with liposomes, association with agents which enhance its uptake into cells, viral transfection. A cell into which a polynucleotide of the present invention has been introduced is a transformed host cell. The polynucleotide can be extrachromosomal or integrated into a chromosome(s) of the host cell. It can be stable or transient. An expression vector is selected for its compatibility with the host cell. Host cells include, mammalian cells, e.g., COS, CV1, BHK, CHO, HeLa, LTK, NIH 3T3, insect cells, such as Sf9(*S. frugipeda*) and Drosophila, bacteria, such as *E.coli*, Streptococcus, bacillus, yeast, such as Sacharomyces, *S. cerevisiae*, fungal cells, plant cells, embryonic or adult stem cells (e.g., mammalian, such as mouse or human).

Expression control sequences are similarly selected for host compatibility and a desired purpose, e.g., high copy number, high amounts, induction, amplification, controlled expression. Other sequences which can be employed include enhancers such as from SV40, CMV, RSV, inducible promoters, cell-type specific elements, or sequences which allow selective or specific cell expression. Promoters that can be used to drive its expression, include, e.g., the endogenous promoter, MMTV, SV40, trp, lac, tac, or T7 promoters for bacterial hosts; or alpha factor, alcohol oxidase, or PGH promoters for yeast. RNA promoters can be used to produced RNA transcripts, such as T7 or SP6. See, e.g., Melton et al., *Polynucleotide Res.*, 12(18):7035–7056, 1984; Dunn and Studier. *J. Mol. Bio.*, 166:477–435, 1984; U.S. Pat. No. 5,891,636; Studier et al., *Gene Expression Technology, Methods in Enzymology*, 85:60–89, 1987. In addition, as discussed above, translational signals (including in-frame insertions) can be included.

When a polynucleotide is expressed as a heterologous gene in a transfected cell line, the gene is introduced into a cell as described above, under effective conditions in which the gene is expressed. The term "heterologous" means that the gene has been introduced into the cell line by the "hand-of-man." Introduction of a gene into a cell line is discussed above. The transfected (or transformed) cell expressing the gene can be lysed or the cell line can be used intact.

For expression and other purposes, a polynucleotide can contain codons found in a naturally-occurring gene, transcript, or cDNA, for example, e.g., as set forth in SEQ ID NO 1, or it can contain degenerate codons coding for the same amino acid sequences. For instance, it may be desirable to change the codons in the sequence to optimize the sequence for expression in a desired host. See, e.g., U.S. Pat. Nos. 5,567,600 and 5,567,862.

A polypeptide according to the present invention can be recovered from natural sources, transformed host cells (culture medium or cells) according to the usual methods, including, detergent extraction (e.g., non-ionic detergent, Triton X-100, CHAPS, octylglucoside, Igepal CA-630), ammonium sulfate or ethanol precipitation, acid extraction, anion or cation exchange chromatography, phosphocellulose chromatography, hydrophobic interaction chromatography, hydroxyapatite chromatography, lectin chromatography, gel electrophoresis. Protein refolding steps can be used, as necessary, in completing the configuration of the mature protein. Finally, high performance liquid chromatography (HPLC) can be employed for purification steps. Another approach is express the polypeptide recombinantly with an affinity tag (Flag epitope, HA epitope, myc epitope, 6xHis, maltose binding protein, chitinase, etc) and then purify by anti-tag antibody-conjugated affinity chromatography.

The present invention also relates to antibodies, and other specific-binding partners, which are specific for polypeptides encoded by polynucleotides of the present invention, e.g., Tbx3-pr408. Antibodies, e.g., polyclonal, monoclonal, recombinant, chimeric, humanized, single-chain, Fab, and fragments thereof, can be prepared according to any desired method. See, also, screening recombinant immunoglobulin libraries (e.g., Orlandi et al., *Proc. Natl. Acad. Sci.*, 86:3833–3837, 1989; Huse et al., *Science*, 256:1275–1281, 1989); in vitro stimulation of lymphocyte populations; Winter and Milstein, *Nature*, 349: 293–299, 1991. The antibodies can be IgM, IgG, subtypes, IgG2a, IgG1, etc. Antibodies, and immune responses, can also be generated by administering naked DNA See, e.g., U.S. Pat. Nos. 5,703,055; 5,589,466; 5,580,859. Antibodies can be used from any source, including, goat, rabbit, mouse, chicken (e.g., IgY; see, Duan, WO/029444 for methods of making antibodies in avian hosts, and harvesting the antibodies from the eggs). An antibody specific for a polypeptide means that the antibody recognizes a defined sequence of amino acids within or including the polypeptide. Other specific binding partners include, e.g., aptamers and PNA. antibodies can be prepared against specific epitopes or domains of Tbx3-pr408, e.g., amino acids 596–608 of SEQ ID NO 2, or peptides comprising amino acids 220–221 (e.g., where the Tbx3-pr408 transcript is to be distinguished from the Tbx3 transcripts which contain the 20-amin acid insertion).

The preparation of polyclonal antibodies is well-known to those skilled in the art. See, for example, Green et al., Production of Polyclonal Antisera, in IMMUNOCHEMICAL PROTOCOLS (Manson, ed.), pages 1–5 (Humana Press 1992); Coligan et al., Production of Polyclonal Antisera in Rabbits, Rats, Mice and Hamsters, in CURRENT PROTOCOLS IN IMMUNOLOGY, section 2.4.1 (1992). The preparation of monoclonal antibodies likewise is conventional. See, for example, Kohler & Milstein, Nature 256:495 (1975); Coligan et al., sections 2.5.1–2.6.7; and Harlow et al., ANTIBODIES: A LABORATORY MANUAL, page 726 (Cold Spring Harbor Pub. 1988).

Antibodies can also be humanized, e.g., where they are to be used therapeutically. Humanized monoclonal antibodies are produced by transferring mouse complementarity determining regions from heavy and light variable chains of the mouse immunoglobulin into a human variable domain, and then substituting human residues in the framework regions of the murine counterparts. The use of antibody components derived from humanized monoclonal antibodies obviates potential problems associated with the immunogenicity of murine constant regions. General techniques for cloning murine immunoglobulin variable domains are described, for example, by Orlandi et al., Proc. Nat'l Acad. Sci. USA 86:3833 (1989), which is hereby incorporated in its entirety by reference. Techniques for producing humanized monoclonal antibodies are described, for example, in U.S. Pat. No. 6,054,297, Jones et al., Nature 321: 522 (1986); Riechmann et al., Nature 332: 323 (1988); Verhoeyen et al., Science 239: 1534 (1988); Carter et al., Proc. Nat'l Acad. Sci. USA 89: 4285 (1992); Sandhu, Crit. Rev. Biotech. 12: 437 (1992); and Singer et al., J. Immunol. 150: 2844 (1993).

Antibodies of the invention also may be derived from human antibody fragments isolated from a combinatorial immunoglobulin library. See, for example, Barbas et al., METHODS: A COMPANION TO METHODS IN ENZYMOLOGY, VOL. 2, page 119 (1991); Winter et al., Ann. Rev. Immunol. 12: 433 (1994). Cloning and expression vectors that are useful for producing a human immunoglobulin phage library can be obtained commercially, for example, from STRATAGENE Cloning Systems (La Jolla, Calif.).

In addition, antibodies of the present invention may be derived from a human monoclonal antibody. Such antibodies are obtained from transgenic mice that have been "engineered" to produce specific human antibodies in response to antigenic challenge. In this technique, elements of the human heavy and light chain loci are introduced into strains of mice derived from embryonic stem cell lines that contain targeted disruptions of the endogenous heavy and light chain loci. The transgenic mice can synthesize human antibodies specific for human antigens and can be used to produce human antibody-secreting hybridomas. Methods for obtaining human antibodies from transgenic mice are described, e.g., in Green et al., Nature Genet. 7:13 (1994); Lonberg et al., Nature 368:856 (1994); and Taylor et al., Int. Immunol. 6:579 (1994).

Antibody fragments of the present invention can be prepared by proteolytic hydrolysis of the antibody or by expression in E. coli of nucleic acid encoding the fragment. Antibody fragments can be obtained by pepsin or papain digestion of whole antibodies by conventional methods. For example, antibody fragments can be produced by enzymatic cleavage of antibodies with pepsin to provide a 5S fragment denoted F(ab').sub.2. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly. These methods are described, for example, by Goldenberg, U.S. Pat. Nos. 4,036,945 and 4,331,647, and references contained therein. These patents are hereby incorporated in their entireties by reference. See also Nisolihoff et al., Arch. Biochem. Biophys. 89:230 (1960); Porter, Biochem. J. 73:119 (1959); Edelman et al, METHODS IN ENZYMOLOGY, VOL. 1, page 422 (Academic Press 1967); and Coligan et al. at sections 2.8.1–2.8.10 and 2.10.1–2.10.4.

Other methods of cleaving antibodies, such as separation of heavy chains to form monovalent light-heavy chain fragments, further cleavage of fragments, or other enzymatic, chemical, or genetic techniques can also be used. For example, Fv fragments comprise an association of V.sub.H and V.sub.L chains. This association may be noncovalent, as described in Inbar et al., Proc. Nat'l Acad. Sci. USA 69:2659 (1972). Alternatively, the variable chains can be linked by an intermolecular disulfide bond or cross-linked by chemicals such as glutaraldehyde. See, e.g., Sandhu, supra. Preferably, the Fv fragments comprise V.sub.H and V.sub.L chains connected by a peptide linker. These single-chain antigen binding proteins (sFv) are prepared by constructing a structural gene comprising nucleic acid sequences encoding the V.sub.H and V.sub.L domains connected by an oligonucleotide. The structural gene is inserted into an expression vector, which is subsequently introduced into a host cell such as *E. coli*. The recombinant host cells synthesize a single polypeptide chain with a linker peptide bridging the two V domains. Methods for producing sFvs are described, for example, by Whitlow et al., METHODS: A COMPANION TO METHODS IN ENZYMOLOGY, VOL. 2, page 97 (1991); Bird etal., Science 242:423–426 (1988); Ladner et al., U.S. Pat. No. 4,946,778; Pack et al., Bio/Technology 11: 1271–77 (1993); and Sandhu, supra.

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells. See, for example, Larrick et al., METHODS: A COMPANION TO METHODS IN ENZYMOLOGY, VOL. 2, page 106 (1991).

The term "antibody" as used herein includes intact molecules as well as fragments thereof, such as Fab, F(ab')2, and Fv which are capable of binding to an epitopic determinant present in Bin1 polypeptide. Such antibody fragments retain some ability to selectively bind with its antigen or receptor. The term "epitope" refers to an antigenic determinant on an antigen to which the paratope of an antibody binds. Epitopic determinants usually consist of chemically active surface groupings of molecules such as amino acids or sugar side chains and usually have specific three dimensional structural characteristics, as well as specific charge characteristics. Antibodies can be prepared against specific epitopes or polypeptide domains.

Antibodies which bind to Tbx3-pr408 polypeptides of the present invention can be prepared using an intact polypeptide or fragments containing small peptides of interest as the immunizing antigen. For example, it may be desirable to produce antibodies that specifically bind to the N- or C-terminal domains of Tbx3-pr408. The polypeptide or peptide used to immunize an animal which is derived from translated cDNA or chemically synthesized which can be conjugated to a carrier protein, if desired. Such commonly used carriers which are chemically coupled to the immunizing peptide include keyhole limpet hemocyanin (KLH), thyroglobulin, bovine serum albumin (BSA), and tetanus toxoid.

Polyclonal or monoclonal antibodies can be further purified, for example, by binding to and elution from a matrix to which the polypeptide or a peptide to which the antibodies were raised is bound. Those of skill in the art will know of various techniques common in the immunology arts for purification and/or concentration of polyclonal antibodies, as well as monoclonal antibodies (See for example, Coligan, et al., Unit 9, Current Protocols in Immunology, Wiley Interscience, 1994, incorporated by reference).

Anti-idiotype technology can also be used to produce invention monoclonal antibodies which mimic an epitope. For example, an anti-idiotypic monoclonal antibody made to a first monoclonal antibody will have a binding domain in the hypervariable region which is the "image" of the epitope bound by the first monoclonal antibody.

Methods of Detecting Polypeptides

Polypeptides coded for by Tbx3-pr408 of the present invention can be detected, visualized, determined, quantitated, etc. according to any effective method. useful methods include, e.g., but are not limited to, immunoassays, RIA (radioimmunassay), ELISA, (enzyme-linked-immunosorbent assay), immunoflourescence, flow cytometry, histology, electron microscopy, light microscopy, in situ assays, immunoprecipitation, Western blot, etc.

Immunoassays may be carried in liquid or on biological support. For instance, a sample (e.g., blood, stool, urine, cells, tissue, cerebral spinal fluid, body fluids, etc.) can be brought in contact with and immobilized onto a solid phase support or carrier such as nitrocellulose, or other solid support that is capable of immobilizing cells, cell particles or soluble proteins. The support may then be washed with suitable buffers followed by treatment with the detectably labeled Tbx3-pr408 specific antibody. The solid phase support can then be washed with a buffer a second time to remove unbound antibody. The amount of bound label on solid support may then be detected by conventional means.

A "solid phase support or carrier" includes any support capable of binding an antigen, antibody, or other specific binding partner. Supports or carriers include glass, polystyrene, polypropylene, polyethylene, dextran, nylon, amylases, natural and modified celluloses, polyacrylamides, and magnetite. A support material can have any structural or physical configuration. Thus, the support configuration may be spherical, as in a bead, or cylindrical, as in the inside surface of a test tube, or the external surface of a rod. Alternatively, the surface may be flat such as a sheet, test strip, etc. Preferred supports include polystyrene beads.

One of the many ways in which gene peptide-specific antibody can be detectably labeled is by linking it to an enzyme and using it in an enzyme immunoassay (EIA). See, e.g., Voller, A., "The Enzyme Linked Immunosorbent Assay (ELISA)," 1978, Diagnostic Horizons 2, 1–7, Microbiological Associates Quarterly Publication, Walkersville, Md.); Voller, A. et al., 1978, J. Clin. Pathol. 31, 507–520; Butler, J. E., 1981, Meth. Enzymol. 73, 482–523; Maggio, E. (ed.), 1980, Enzyme Immunoassay, CRC Press, Boca Raton, Fla. The enzyme which is bound to the antibody will react with an appropriate substrate, preferably a chromogenic substrate, in such a manner as to produce a chemical moiety that can be detected, for example, by spectrophotometric, fluorimetric or by visual means. Enzymes that can be used to detectably label the antibody include, but are not limited to, malate dehydrogenase, staphylococcal nuclease, delta-5-steroid isomerase, yeast alcohol dehydrogenase, .alpha.-glycerophosphate, dehydrogenase, triose phosphate isomerase, horseradish peroxidase, alkaline phosphatase, asparaginase, glucose oxidase, .beta.-galactosidase, ribonuclease, urease, catalase, glucose-6-phosphate dehydrogenase, glucoamylase and acetylcholinesterase. The detection can be accomplished by calorimetric methods that employ a chromogenic substrate for the enzyme. Detection may also be accomplished by visual comparison of the extent of enzymatic reaction of a substrate in comparison with similarly prepared standards.

Detection may also be accomplished using any of a variety of other immunoassays. For example, by radioactively labeling the antibodies or antibody fragments, it is possible to detect Tbx3-pr408 peptides through the use of a radioimmunoassay (RIA). See, e.g., Weintraub, B., Principles of Radioimmunoassays, Seventh Training Course on Radioligand Assay Techniques, The Endocrine Society, March, 1986. The radioactive isotope can be detected by such means as the use of a gamma counter or a scintillation counter or by autoradiography.

It is also possible to label the antibody with a fluorescent compound. When the fluorescently labeled antibody is exposed to light of the proper wave length, its presence can then be detected due to fluorescence. Among the most commonly used fluorescent labeling compounds are fluorescein isothiocyanate, rhodamine, phycoerythrin, phycocyanin, allophycocyanin, o-phthaldehyde and fluorescamine. The antibody can also be detectably labeled using fluorescence emitting metals such as those in the lanthanide series. These metals can be attached to the antibody using such metal chelating groups as diethylenetriaminepentacetic acid (DTPA) or ethylenediaminetetraacetic acid (EDTA).

The antibody also can be detectably labeled by coupling it to a chemiluminescent compound. The presence of the chemiluminescent-tagged antibody is then determined by detecting the presence of luminescence that arises during the course of a chemical reaction. Examples of useful chemiluminescent labeling compounds are luminol, isoluminol, theromatic acridinium ester, imidazole, acridinium salt and oxalate ester.

Likewise, a bioluminescent compound may be used to label the antibody of the present invention. Bioluminescence is a type of chemiluminescence found in biological systems in which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

Diagnostic

The present invention also relates to methods and compositions for diagnosing a developmental disorder, or determining susceptibility to a disorder, using polynucleotides, polypeptides, and specific-binding partners of the present invention to detect, assess, determine, etc., Tbx3-pr408. In such methods, the gene can serve as a marker for the disorder, e.g., where the gene, when mutant, is a direct cause of the disorder; where the gene is affected by another gene(s) which is directly responsible for the disorder, e.g., when the gene is part of the same signaling pathway as the directly responsible gene; and, where the gene is chromosomally linked to the gene(s) directly responsible for the disorder, and segregates with it. Many other situations are possible. To detect, assess, determine, etc., a probe specific for the gene can be employed as described above and below. Any method of detecting and/or assessing the gene can be used, including detecting expression of the gene using polynucleotides, antibodies, or other specific-binding partners.

The present invention relates to methods of diagnosing a disorder associated with Tbx3-pr408 (e.g., of the prostate, heart, muscle, lung, or adrenal gland), or determining a subject's susceptibility to such disorder, comprising, e.g., assessing the expression of Tbx3-pr408 in a tissue sample comprising tissue or cells suspected of having the disorder.

The phrase "diagnosing" indicates that it is determined whether the sample has the disorder. A "disorder" means, e.g., any abnormal condition as in a disease or malady. "Determining a subject's susceptibility to a disease or disorder" indicates that the subject is assessed for whether s/he is predisposed to get such a disease or disorder, where the predisposition is indicated by abnormal expression of the gene (e.g., gene mutation, gene expression pattern is not normal, etc.). Predisposition or susceptibility to a disease may result when a such disease is influenced by epigenetic, environmental, etc., factors. This includes prenatal screening where samples from the fetus or embryo (e.g., via amniocentesis or CV sampling) are analyzed for the expression of the gene.

By the phrase "assessing expression of Tbx3-pr408," it is meant that the functional status of the gene is evaluated. This includes, but is not limited to, measuring expression levels of said gene, determining the genomic structure of said gene, determining the mRNA structure of transcripts from said gene, or measuring the expression levels of polypeptide coded for by said gene. Thus, the term "assessing expression" includes evaluating the all aspects of the transcriptional and translational machinery of the gene. For instance, if a promoter defect causes, or is suspected of causing, the disorder, then a sample can be evaluated (i.e., "assessed") by looking (e.g., sequencing or restriction mapping) at the promoter sequence in the gene, by detecting transcription products (e.g., RNA), by detecting translation product (e.g., polypeptide). Any measure of whether the gene is functional can be used, including, polypeptide, polynucleotide, and functional assays for the gene's biological activity.

In making the assessment, it can be useful to compare the results to a normal gene, e.g., a gene which is not associated with the disorder. The nature of the comparison can be determined routinely, depending upon how the assessing is accomplished. If, for example, the mRNA levels of a sample is detected, then the mRNA levels of a normal can serve as a comparison, or a gene which is known not to be affected by the disorder. Methods of detecting mRNA are well known, and discussed above, e.g., but not limited to, Northern blot analysis, polymerase chain reaction (PCR), reverse transcriptase PCR, RACE PCR, etc. Similarly, if polypeptide production is used to evaluate the gene, then the polypeptide in a normal tissue sample can be used as a comparison, or, polypeptide from a different gene whose expression is known not to be affected by the disorder. These are only examples of how such a method could be carried out.

Assessing the effects of therapeutic and preventative interventions (e.g., administration of a drug, chemotherapy, radiation, etc.) on disorders is a major effort in drug discovery, clinical medicine, and pharmacogenomics. The evaluation of therapeutic and preventative measures, whether experimental or already in clinical use, has broad applicability, e.g., in clinical trials, for monitoring the status of a patient, for analyzing and assessing animal models, and in any scenario involving cancer treatment and prevention. Analyzing the expression profiles of polynucleotides of the present invention can be utilized as a parameter by which interventions are judged and measured. Treatment of a disorder can change the expression profile in some manner which is prognostic or indicative of the drug's effect on it. Changes in the profile can indicate, e.g., drug toxicity, return to a normal level, etc. Accordingly, the present invention also relates to methods of monitoring or assessing a therapeutic or preventative measure (e.g., chemotherapy, radiation, anti-neoplastic drugs, antibodies, etc.) in a subject having a disorder, or, susceptible to such a disorder, comprising, e.g., detecting the expression levels of Tbx3-pr408. A subject can be a cell-based assay system, non-human animal model, human patient, etc. Detecting can be accomplished as described for the methods-above and below. By "therapeutic or preventative intervention," it is meant, e.g., a drug administered to a patient, surgery, radiation, chemotherapy, and other measures taken to prevent, treat, or diagnose a disorder.

The present invention also relates to methods of detecting Tbx transcripts in a tissue sample, comprising, e.g., assessing the expression of a Tbx3-pr408 transcript in a tissue sample, and assessing the expression of other transcripts of the Tbx3 gene, such as those represented by NM_005996 (SEQ ID NO 3), XM_016321 (SEQ ID NO 4), and NM_016569 (SEQ ID NO 5). Tbx3 transcripts which contain about a 20 amino acid insertion at about amino acid 220 are referred to "Tbx3 transcripts comprising a T box insertion." Examples are NM_005996 (SEQ ID NO 3) and XM_016321 (SEQ ID NO 4). Assessing can be accomplished as described above. This method can be used to determine the relative levels of Tbx3-pr408 as compared to other Tbx3 transcripts. For instance, as described above, Tbx3-pr408 is more abundant in most tissues than NM_005996 or XM_016321. Patients having mammary-ulnar syndrome can be assessed for the relative levels of both transcript types. If PCR is used to determine mRNA expression, the following primers can be used which span the insertion, e.g., forward primer having the sequence of about 1023–1048 (SEQ ID NO 1), and a reverse primer which is complementary to the sequence of about 1230–1255. If both transcripts are present in the sample, two different bands will be detected, the larger corresponding to NM_005996 or XM_016321, and the smaller to Tbx3-pr408.

Identifying Agent Methods

The present invention relates to compositions and methods of modulating Tbx3-pr48 gene or polypeptide. Assays can be performed on whole cells, lysates, isolated Tbx3-pr408, etc.

For example, the present invention also relates to methods of identifying agents that modulate the expression of Tbx3-pr408 in a cell population, comprising, in any effective order, one or more of the following steps, e.g., contacting a cell population with a test agent under conditions effective for said test agent to modulate the expression of Tbx3-pr408 in said cell population, and determining whether said test agent modulates said Tbx3-pr408. An agent can modulate expression of Tbx3-pr408 at any level, including transcription, translation, and/or perdurance of the nucleic acid or polypeptide (e.g., degradation, stability, etc.) product in the cell.

In addition, the present invention also relates to methods of identifying agents that modulate the biological activity of Tbx3-pr408 polypeptide in a cell population, lysate, etc., comprising, in any effective order, one or more of the following steps, e.g., contacting said polypeptide with a test agent under conditions effective for said test agent to modulate the biological activity of said polypeptide, and determining whether said test agent modulates said biological activity.

Contacting the cell population with the test agent can be accomplished by any suitable method and/or means that places the agent in a position to functionally control expression or biological activity of Tbx3-pr408 present in cells within the population, or in the sample mixture. Functional control indicates that the agent can exert its physiological effect on the cell through whatever mechanism it works. The choice of the method and/or means can depend upon the nature of the agent and the condition and type of the cell population (such as, in vivo, in vitro, organ explants, etc.). For instance, if the cell population is an in vitro cell culture, the agent can be contacted with the cells by adding it directly into the culture medium. If the agent cannot dissolve readily in an aqueous medium, it can be incorporated into liposomes, or another lipophilic carrier, and then administered to the cell culture. Contact can also be facilitated by incorporation of agent with carriers and delivery molecules and complexes, by injection, by infusion, etc.

After the agent has been administered in such a way that it can gain access to the cells or polypeptide, it can be determined whether the test agent modulates Tbx3-pr408 expression or biological activity. Modulation can be of any type, quality, or quantity, e.g., increase, facilitate, enhance, up-regulate, stimulate, activate, amplify, augment, induce, decrease, down-regulate, diminish, lessen, reduce, etc. The modulatory quantity can also encompass any value, e.g., 1%, 5%, 10%, 50%, 75%, 1-fold, 2-fold, 5-fold, 10-fold, 100-fold, etc. To modulate Tbx3-pr408 expression means, e.g., that the test agent has an effect on its expression, e.g., to effect the amount of transcription, to effect RNA splicing, to effect translation of the RNA into polypeptide, to effect RNA or polypeptide stability, to effect polyadenylation or other processing of the RNA, to effect post-transcriptional or post-translational processing, etc. To modulate biological activity means, e.g., that the activity of the polypeptide is changed in comparison to its normal activity in the absence of the agent. This effect includes, increase, decrease, block, inhibit, enhance, etc. Biological activities of Tbx3-pr408 included, e.g., transcription regulatory activity, DNA-binding activity, etc. Assays for measuring these activities were discussed previously.

A test agent can be of any molecular composition, e.g., chemical compounds, biomolecules, such as polypeptides, lipids, nucleic acids (e.g., antisense to a polynucleotide sequence selected from SEQ ID NO 1), carbohydrates, antibodies, ribozymes, double-stranded RNA, etc. For example, if a polypeptide to be modulated is a cell-surface molecule, a test agent can be an antibody that specifically recognizes it and, e.g., causes the polypeptide to be internalized, leading to its down regulation on the surface of the cell. Such an effect does not have to be permanent, but can require the presence of the antibody to continue the down-regulatory effect. Antisense Tbx3-pr408 can also be used as test agents to modulate gene expression.

The entire Tbx3-pr408 polypeptide can be used, or biologically-active fragments thereof. If transcriptional activity is being measured, then a biologically-active fragment would be one that retains transcriptional regulatory activity, and so on. In some cases, biologically-active fragments can comprise Tbx3-pr408 specific sequence. By this, it is meant that fragments common to other Tbx3 transcripts (e.g., NM_005996, XM_016321, and NM_016569) are excluded. An example of such a fragment would comprise amino acids from about 596–608, e.g., 1–650, 50–650, 50–723, 300–650 (e.g., fragments deleting the DNA-binding domain), 300–723, etc.

Therapeutics

Selective polynucleotides, polypeptides, and specific-binding partners thereto, can be utilized in therapeutic applications, especially to treat diseases and conditions of associated with Tbx-pr408, e.g., mammary-ulnar disease. Useful methods include, but are not limited to, immunotherapy (e.g., using specific-binding partners to polypeptides), vaccination (e.g., using a selective polypeptide or a naked DNA encoding such polypeptide), protein or polypeptide replacement therapy, gene therapy (e.g., germ-line correction, antisense), etc.

Various immunotherapeutic approaches can be used. For instance, unlabeled antibody that specifically recognizes a tissue-specific antigen can be used to stimulate the body to destroy or attack the cancer, to cause down-regulation, to produce complement-mediated lysis, to inhibit cell growth, etc., of target cells which display the antigen, e.g., analogously to how c-erbB-2 antibodies are used to treat breast cancer. In addition, antibody can be labeled or conjugated to enhance its deleterious effect, e.g., with radionuclides and other energy emitting entitities, toxins, such as ricin, exotoxin A (ETA), and diphtheria, cytotoxic or cytostatic agents, immunomodulators, chemotherapeutic agents, etc. See, e.g., U.S. Pat. No. 6,107,090.

An antibody or other specific-binding partner can be conjugated to a second molecule, such as a cytotoxic agent, and used for targeting the second molecule to a tissue-antigen positive cell (Vitetta, E. S. et al., 1993, Immunotoxin therapy, in DeVita, Jr., V. T. et al., eds, Cancer: Principles and Practice of Oncology, 4th ed., J. B. Lippincott Co., Philadelphia, 2624–2636). Examples of cytotoxic agents include, but are not limited to, antimetabolites, alkylating agents, anthracyclines, antibiotics, anti-mitotic agents, radioisotopes and chemotherapeutic agents. Further examples of cytotoxic agents include, but are not limited to ricin, doxorubicin, daunorubicin, taxol, ethidium bromide, mitomycin, etoposide, tenoposide, vincristine, vinblastine, colchicine, dihydroxy anthracin dione, actinomycin D, 1-dehydrotestosterone, diptheria toxin, Pseudomonas exotoxin (PE) A, PE40, abrin, elongation factor-2 and glucocorticoid. Techniques for conjugating therapeutic agents to antibodies are well.

In addition to immunotherapy, polynucleotides and polypeptides can be used as targets for non-immunotherapeutic applications, e.g., using compounds which interfere with function, expression (e.g., antisense as a therapeutic agent), assembly, etc. RNA interference can be used in vivtro and in vivo to silence Tbx3-pr408 when its expression contributes to a disease (but also for other purposes, e.g., to identify the gene's function to change a developmental pathway of a cell, etc.). See, e.g., Sharp and Zamore, Science, 287:2431–2433, 2001; Grishok et al., Science, 287:2494, 2001.

Delivery of therapeutic agents can be achieved according to any effective method, including, liposomes, viruses, plasmid vectors, bacterial delivery systems, orally, systemically, etc. Therapeutic agents of the present invention can be administered in any form by any effective route, including, e.g., oral, parenteral, enteral, intraperitoneal, topical, transdermal (e.g., using any standard patch), ophthalmic, nasally, local, non-oral, such as aerosal, inhalation, subcutaneous, intramuscular, buccal, sublingual, rectal, vaginal, intra-arterial, and intrathecal, etc. They can be administered alone, or in combination with any ingredient(s), active or inactive.

In addition to therapeutics, per se, the present invention also relates to methods of treating a disease showing altered expression of Tbx3-pr408, comprising, e.g., administering to a subject in need thereof a therapeutic agent which is effective for regulating expression of said Tbx3-pr408 and/ or which is effective in treating said disease. The term "treating" is used conventionally, e.g., the management or care of a subject for the purpose of combating, alleviating, reducing, relieving, improving the condition of, etc., of a disease or disorder. By the phrase "altered expression," it is meant that the disease is associated with a mutation in the gene, or any modification to the gene (or corresponding product) which affects its normal function. Thus, expression of Tbx3-pr408 refers to, e.g., transcription, translation, splicing, stability of the mRNA or protein product, activity of the gene product, differential expression, etc.

Any agent which "treats" the disease can be used. Such an agent can be one which regulates the expression of the Tbx3-pr408. Expression refers to the same acts already mentioned, e.g. transcription, translation, splicing, stability of the mRNA or protein product, activity of the gene product, differential expression, etc. For instance, if the condition was a result of a complete deficiency of the gene product, administration of gene product to a patient would be said to treat the disease and regulate the gene's expression. Many other possible situations are possible, e.g., where the gene is aberrantly expressed, and the therapeutic agent regulates the aberrant expression by restoring its normal expression pattern.

Antisense

Antisense polynucleotide (e.g., RNA) can also be prepared from a polynucleotide according to the present invention, preferably an anti-sense to a sequence of SEQ ID NO 1. Antisense polynucleotide can be used in various ways, such as to regulate or modulate expression of the polypeptides they encode, e.g., inhibit their expression, for in situ hybridization, for therapeutic purposes, for making targeted mutations (in vivo, triplex, etc.) etc. For guidance on administering and designing anti-sense, see, e.g., U.S. Pat. Nos. 6,200,960, 6,200,807, 6,197,584, 6,190,869, 6,190,661, 6,187,587, 6,168,950, 6,153,595, 6,150,162, 6,133,246, 6,117,847, 6,096,722, 6,087,343, 6,040,296, 6,005,095, 5,998,383, 5,994,230, 5,891,725, 5,885,970, and 5,840,708. An antisense polynucleotides can be operably linked to an expression control sequence. A total length of about 35 bp can be used in cell culture with cationic liposomes to facilitate cellular uptake, but for in vivo use, preferably shorter oligonucleotides are administered, e.g. nucleotides.

Antisense polynucleotides can comprise modified, nonnaturally-occurring nucleotides and linkages between the nucleotides (e.g., modification of the phosphate-sugar backbone; methyl phosphonate, phosphorothioate, or phosphorodithioate linkages; and 2'-O-methyl ribose sugar units), e.g., to enhance in vivo or in vitro stability, to confer nuclease resistance, to modulate uptake, to modulate cellular distribution and compartmentalization, etc. Any effective nucleotide or modification can be used, including those already mentioned, as known in the art, etc., e.g., disclosed in U.S. Pat. Nos. 6,133,438; 6,127,533; 6,124,445; 6,121,437; 5,218,103 (e.g., nucleoside thiophosphoramidites); 4,973,679; Sproat et al., "2'-O-Methyloligoribonucleotides: synthesis and applications," Oligonucleotides and Analogs A Practical Approach, Eckstein (ed.), IRL Press, Oxford, 1991, 49–86; Iribarren et al., "2'-O-Alkyl Oligoribonucleotides as Antisense Probes," Proc. Natl. Acad. Sci. USA, 1990, 87, 7747–7751; Cotton et al., "2'-O-methyl, 2'-O-ethyl oligoribonucleotides and phosphorothioate oligodeoxyribonucleotides as inhibitors of the in vitro U7 snRNP-dependent mRNA processing event," Nucl. Acids Res., 1991, 19, 2629–2635.

Arrays

The present invention also relates to an ordered array of polynucleotide probes and specific-binding partners (e.g., antibodies) for detecting the expression of Tbx3-pr408 in a sample, comprising, one or more polynucleotide probes or specific binding partners associated with a solid support, wherein each probe is specific for Tbx3-pr408, and the probes comprise a nucleotide sequence of SEQ ID NO 1 which is specific for said gene, a nucleotide sequence having sequence identity to SEQ ID NO 1 which is specific for said gene or polynucleotide, or complements thereto, or a specific-binding partner which is specific for Tbx3-pr408.

The phrase "ordered array" indicates that the probes are arranged in an identifiable or position-addressable pattern, e.g., such as the arrays disclosed in U.S. Pat. Nos. 6,156,501, 6,077,673, 6,054 ,270, 5,723,320, 5,700,637, WO09919711, WO00023803. The probes are associated with the solid support in any effective way. For instance, the probes can be bound to the solid support, either by polymerizing the probes on the substrate, or by attaching a probe to the substrate. Association can be, covalent, electrostatic, noncovalent, hydrophobic, hydrophilic, noncovalent, coordination, adsorbed, absorbed, polar, etc. When fibers or hollow filaments are utilized for the array, the probes can fill the hollow orifice, be absorbed into the solid filament, be attached to the surface of the orifice, etc. Probes can be of any effective size, sequence identity, composition, etc., as already discussed.

Transgenic Animals

The present invention also relates to transgenic animals comprising Tbx3-pr408 genes. Such genes, as discussed in more detail below, include, but are not limited to, functionally-disrupted genes, mutated genes, ectopically or selectively-expressed genes, inducible or regulatable genes, etc. These transgenic animals can be produced according to any suitable technique or method, including homologous recombination, mutagenesis (e.g., ENU, Rathkolb et al., *Exp. Physiol.*, 85(6):635–644, 2000), and the tetracycline-regulated gene expression system (e.g., U.S. Pat. No. 6,242,667). The term "gene" as used herein includes any part of a gene, i.e., regulatory sequences, promoters, enhancers, exons, introns, coding sequences, etc. The Tbx3-pr408 nucleic acid present in the construct or transgene can be naturally-occurring wild-type, polymorphic, or mutated.

Along these lines, polynucleotides of the present invention can be used to create transgenic animals, e.g. a non-human animal, comprising at least one cell whose genome comprises a functional disruption of Tbx3-pr408. By the phrases "functional disruption" or "functionally disrupted," it is meant that the gene does not express a biologically-active product. It can be substantially deficient in at least one functional activity coded for by the gene. Expression of a polypeptide can be substantially absent, i.e., essentially undetectable amounts are made. However, polypeptide can also be made, but which is deficient in activity, e.g., where only an amino-terminal portion of the gene product is produced.

The transgenic animal can comprise one or more cells. When substantially all its cells contain the engineered gene, it can be referred to as a transgenic animal "whose genome comprises" the engineered gene. This indicates that the endogenous gene loci of the animal has been modified and substantially all cells contain such modification.

Functional disruption of the gene can be accomplished in any effective way, including, e.g., introduction of a stop codon into any part of the coding sequence such that the resulting polypeptide is biologically inactive (e.g., because it lacks a catalytic domain, a ligand binding domain, etc.), introduction of a mutation into a promoter or other regulatory sequence that is effective to turn it off, or reduce transcription of the gene, insertion of an exogenous sequence into the gene which inactivates it (e.g., which disrupts the production of a biologically-active polypeptide or which disrupts the promoter or other transcriptional machinery), deletion of sequences from the Tbx3-pr408 gene, etc. Examples of transgenic animals having functionally disrupted genes are well known, e.g., as described in U.S. Pat. Nos. 6,239,326, 6,225,525, 6,207,878, 6,194,633, 6,187,992, 6,180,849, 6,177,610, 6,100,445, 6,087,555, 6,080,910, 6,069,297, 6,060,642, 6,028,244, 6,013,858, 5,981,830, 5,866,760, 5,859,314, 5,850,004, 5,817,912, 5,789,654, 5,777,195, and 5,569,824. A transgenic animal which comprises the functional disruption can also be referred to as a "knock-out" animal, since the biological activity of its Tbx3-pr408 genes has been "knocked-out." Knock-outs can be homozygous or heterozygous.

For creating functional disrupted genes, and other gene mutations, homologous recombination technology is of special interest since it allows specific regions of the genome to be targeted. Using homologous recombination methods, genes can be specifically-inactivated, specific mutations can be introduced, and exogenous sequences can be introduced at specific sites. These methods are well known in the art, e.g., as described in the patents above. See, also, Robertson, *Biol. Reproduc.*, 44(2):238–245, 1991. Generally, the genetic engineering is performed in an embryonic stem (ES) cell, or other pluripotent cell line (e.g., adult stem cells, EG cells), and that genetically-modified cell (or nucleus) is used to create a whole organism. Nuclear transfer can be used in combination with homologous recombination technologies.

For example, the Tbx3-pr408 locus can be disrupted in mouse ES cells using a positive-negative selection method (e.g., Mansour et al., *Nature*, 336:348–352, 1988). In this method, a targeting vector can be constructed which comprises a part of the gene to be targeted. A selectable marker, such as neomycin resistance genes, can be inserted into a Tbx3-pr408 exon present in the targeting vector, disrupting it. When the vector recombines with the ES cell genome, it disrupts the function of the gene. The presence in the cell of the vector can be determined by expression of neomycin resistance. See, e.g., U.S. Pat. No. 6,239,326. Cells having at least one functionally disrupted gene can be used to make chimeric and germline animals, e.g., animals having somatic and/or germ cells comprising the engineered gene. Homozygous knock-out animals can be obtained from breeding heterozygous knock-out animals. See, e.g., U.S. Pat. No. 6,225,525.

A transgenic animal, or animal cell, lacking one or more functional Tbx3-pr408 genes can be useful in a variety of applications, including, as an animal model for mammary-ulnar disease, and any of the utilities mentioned in any issued U.S. Patent on transgenic animals, including, U.S. Pat. Nos. 6,239,326, 6,225,525, 6,207,878, 6,194,633, 6,187,992, 6,180,849, 6,177,610, 6,100,445, 6,087,555, 6,080,910, 6,069,297, 6,060,642, 6,028,244, 6,013,858, 5,981,830, 5,866,760, 5,859,314, 5,850,004, 5,817,912, 5,789,654, 5,777,195, and 5,569,824.

The present invention also relates to non-human, transgenic animal whose genome comprises recombinant Tbx3-pr408 nucleic acid operatively linked to an expression control sequence effective to express said coding sequence, e.g., in heart, prostate, lung, adrenal, testes, and/or muscle. Such a transgenic animal can also be referred to as a "knock-in" animal since an exogenous gene has been introduced, stably, into its genome.

A recombinant Tbx3-pr408 nucleic acid refers to a gene which has been introduced into a target host cell and optionally modified, such as cells derived from animals, plants, bacteria, yeast, etc. A recombinant Tbx3-pr408 includes completely synthetic nucleic acid sequences, semi-synthetic nucleic acid sequences, sequences derived from natural sources, and chimeras thereof. "Operable linkage" has the meaning used through the specification, i.e., placed in a functional relationship with another nucleic acid. When a gene is operably linked to an expression control sequence, as explained above, it indicates that the gene (e.g., coding sequence) is joined to the expression control sequence (e.g., promoter) in such a way that facilitates transcription and translation of the coding sequence. As described above, the phrase "genome" indicates that the genome of the cell has been modified. In this case, the recombinant Tbx3-pr408 has been stably integrated into the genome of the animal. The Tbx3-pr408 nucleic acid in operable linkage with the expression control sequence can also be referred to as a construct or transgene.

Any expression control sequence can be used depending on the purpose. For instance, if selective expression is desired, then expression control sequences which limit its expression can be selected. These include, e.g., tissue or cell-specific promoters, introns, enhancers, etc. For various methods of cell and tissue-specific expression, see, e.g., U.S. Pat. Nos. 6,215,040, 6,210,736, and 6,153,427. These also include the endogenous promoter, i.e., the coding sequence can be operably linked to its own promoter. Inducible and regulatable promoters can also be utilized.

The present invention also relates to a transgenic animal which contains a functionally disrupted and a transgene stably integrated into the animals genome. Such an animal can be constructed using combinations any of the above- and below-mentioned methods. Such animals have any of the aforementioned uses, including permitting the knock-out of the normal gene and its replacement with a mutated gene. Such a transgene can be integrated at the endogenous gene locus so that the functional disruption and "knock-in" are carried out in the same step.

In addition to the methods mentioned above, transgenic animals can be prepared according to known methods, including, e.g., by pronuclear injection of recombinant genes into pronuclei of 1-cell embryos, incorporating an artificial yeast chromosome into embryonic stem cells, gene targeting methods, embryonic stem cell methodology, cloning methods, nuclear transfer methods. See, also, e.g., U.S. Pat. Nos. 4,736,866; 4,873,191; 4,873,316; 5,082,779; 5,304,489; 5,174,986; 5,175,384; 5,175,385; 5,221,778; Gordon et al., Proc. Natl. Acad. Sci., 77:7380–7384, 1980; Palmiter et al., Cell, 41:343–345, 1985; Palmiter et al., Ann. Rev. Genet., 20:465–499, 1986; Askew et al., Mol. Cell. Bio., 13:4115–4124, 1993; Games et al. Nature, 373:523–527, 1995; Valancius and Smithies, Mol. Cell. Bio., 11: 1402–1408, 1991; Stacey et al., Mol. Cell. Bio., 14:1009–1016, 1994; Hasty et al., Nature, 350:243–246, 1995; Rubinstein et al., Nucl. Acid Res., 21:2613–2617, 1993; Cibelli et al., Science, 280:1256–1258, 1998. For guidance on recombinase excision systems, see, e.g., U.S. Pat. Nos. 5,626,159, 5,527,695, and 5,434,066. See also, Orban, P. C., et al., "Tissue-and Site-Specific DNA Recombination in Transgenic Mice," Proc. Natl. Acad. Sci. USA, 89:6861–6865 (1992); O'Gorman, S., et al., "Recombinase-Mediated Gene Activation and Site-Specific Integration in Mammalian Cells," Science, 251:1351–1355 (1991); Sauer, B., et al., "Cre-stimulated recombination at loxP-Containing DNA sequences placed into the mammalian genome," Polynucleotides Research, 17(1):147–161 (1989); Gagneten, S. et al. (1997) Nucl. Acids Res. 25:3326–3331; Xiao and Weaver (1997) Nucl. Acids Res. 25:2985–2991; Agah, R. et al. (1997) J. Clin. Invest. 100:169–179; Barlow, C. et al. (1997) Nucl. Acids Res. 25:2543–2545; Araki, K. et al. (1997) Nucl. Acids Res. 25:868–872; Mortensen, R. N. et al. (1992) Mol. Cell. Biol. 12:2391–2395 (G418 escalation method); Lakhlani, P. P. et al. (1997) Proc. Natl. Acad. Sci. USA 94:9950–9955 ("hit and run"); Westphal and Leder (1997) Curr. Biol. 7:530–533 (transposon-generated "knock-out" and "knock-in"); Templeton, N. S. et al. (1997) Gene Ther. 4:700–709 (methods for efficient gene targeting, allowing for a high frequency of homologous recombination events, e.g., without selectable markers); PCT International Publication WO93/22443 (functionally-disrupted).

A polynucleotide according to the present invention can be introduced into any non-human animal, including a non-human mammal, mouse (Hogan et al., *Manipulating the Mouse Embryo: A Laboratory Manual, Cold Spring Harbor Laboratoty*, Cold Spring Harbor, New York, 1986), pig (Hammeret al., Nature, 315:343–345, 1985), sheep (Hammer et al., Nature, 315:343–345, 1985), cattle, rat, or primate. See also, e.g., Church, 1987, Trends in Biotech. 5:13–19; Clark et al., Trends in Biotech. 5:20–24, 1987); and DePamphilis et al., BioTechniques, 6:662–680, 1988. Transgenic animals can be produced by the methods described in U.S. Pat. No. 5,994,618, and utilized for any of the utilities described therein.

Database

The present invention also relates to electronic forms of polynucleotides, polypeptides, etc., of the present invention, including computer-readable medium (e.g., magnetic, optical, etc., stored in any suitable format, such as flat files or hierarchical files) which comprise such sequences, or fragments thereof, e-commerce-related means, etc. Along these lines, the present invention relates to methods of retrieving gene sequences from a computer-readable medium, comprising, one or more of the following steps in any effective order, e.g., selecting a cell or gene expression profile, e.g., a profile that specifies that said gene is differentially expressed in, e.g., heart, prostate, and lung, and retrieving said differentially expressed gene sequences, where the gene sequences consist of the genes represented by SEQ ID NOS 1 and 2.

A "gene expression profile" means the list of tissues, cells, etc., in which a defined gene is expressed (i.e, transcribed and/or translated). A "cell expression profile" means the genes which are expressed in the particular cell type. The profile can be a list of the tissues in which the gene is expressed, but can include additional information as well, including level of expression (e.g., a quantity as compared or normalized to a control gene), and information on temporal (e.g., at what point in the cell-cycle or developmental program) and spatial expression. By the phrase "selecting a gene or cell expression profile," it is meant that a user decides what type of gene or cell expression pattern he is interested in retrieving, e.g., he may require that the gene is differentially expressed in a tissue, or he may require that the gene is not expressed in blood, but must be expressed in prostate. Any pattern of expression preferences may be selected. The selecting can be performed by any effective method. In general, "selecting" refers to the process in which a user forms a query that is used to search a database of gene expression profiles. The step of retrieving involves searching for results in a database that correspond to the query set forth in the selecting step. Any suitable algorithm can be utilized to perform the search query, including algorithms that look for matches, or that perform optimization between query and data. The database is information that has been stored in an appropriate storage medium, having a suitable computer-readable format. Once results are retrieved, they can be displayed in any suitable format, such as HTML.

For instance, the user may be interested in identifying genes that are differentially expressed in prostate and heart. He may not care whether small amounts of expression occur in other tissues, as long as such genes are not expressed in peripheral blood lymphocytes. A query is formed by the user to retrieve the set of genes from the database having the desired gene or cell expression profile. Once the query is inputted into the system, a search algorithm is used to interrogate the database, and retrieve results.

Advertising, Licensing, etc., Methods

The present invention also relates to methods of advertising, licensing, selling, purchasing, brokering, etc., genes, polynucleotides, specific-binding partners, antibodies, etc., of the present invention. Methods can comprises, e.g., displaying a Tbx3-pr408 gene, Tbx3-pr408 polypeptide, or antibody specific for Tbx3-pr408 in a printed or computer-readable medium (e.g., on the Web or Internet), accepting an offer to purchase said gene, polypeptide, or antibody.

Other

A polynucleotide, probe, polypeptide, antibody, specific-binding partner, etc., according to the present invention can be isolated. The term "isolated" means that the material is in a form in which it is not found in its original environment or in nature, e.g., more concentrated, more purified, separated from component, etc. An isolated polynucleotide includes, e.g., a polynucleotide having the sequenced separated from the chromosomal DNA found in a living animal, e.g., as the complete gene, a transcript, or a cDNA. This polynucleotide can be part of a vector or inserted into a chromosome (by specific gene-targeting or by random integration at a position other than its normal position) and still be isolated in that it is not in a form that is found in its natural environment. A polynucleotide, polypeptide, etc., of the present invention can also be substantially purified. By substantially purified, it is meant that polynucleotide or polypeptide is separated and is essentially free from other polynucleotides or polypeptides, i.e., the polynucleotide or polypeptide is the primary and active constituent. A polynucleotide can also be a recombinant molecule. By "recombinant," it is meant that the polynucleotide is an arrangement or form which does not occur in nature. For instance, a recombinant molecule comprising a promoter sequence would not encompass the naturally-occurring gene, but would include the promoter operably linked to a coding sequence not associated with it in nature, e.g., a reporter gene, or a truncation of the normal coding sequence.

The term "marker" is used herein to indicate a means for detecting or labeling a target. A marker can be a polynucleotide (usually referred to as a "probe"), polypeptide (e.g., an antibody conjugated to a detectable label), PNA, or any effective material.

The topic headings set forth above are meant as guidance where certain information can be found in the application, but are not intended to be the only source in the application where information on such topic can be found. Reference materials For other aspects of the polynucleotides, reference is made to standard textbooks of molecular biology. See, e.g., Hames et al., *Polynucleotide Hybridization*, IL Press, 1985; Davis et al., *Basic Methods in Molecular Biology*, Elsevir Sciences Publishing, Inc., New York, 1986; Sambrook et al., *Molecular Cloning*, CSH Press, 1989; Howe, *Gene Cloning and Manipulation*, Cambridge University Press, 1995; Ausubel et al., *Current Protocols in Molecular Biology*, John Wiley & Sons, Inc., 1994–1998.

The preceding description, utilize the present invention to its fullest extent. The preceding preferred specific embodiments are, therefore, to be construed as merely illustrative, and not limiting the remainder of the disclosure in any way whatsoever. The entire disclosure of all applications, patents and publications, cited above and in the figures are hereby incorporated by reference in their entirety.

What is claimed is:

1. An isolated polynucleotide comprising,
   a polynucleotide sequence which codes without interruption for Tbx3-pr408 which has the amino acid sequence set forth in SEQ ID NO 2, or a complement thereto.

2. A mammalian cell, comprising an exogenous polynucleotide of claim 1.

3. An isolated polynucleotide of claim 1, having the polynucleotide sequence set forth in SEQ ID NO 1, or a complement thereto.

4. An isolated polynucleotide of claim 1, further comprising an expression control sequence operably linked to said sequence coding for Tbx3-pr408.

5. An isolated polynucleotide of claim 3, further comprising an expression control sequence operably linked to said sequence coding for Tbx3-pr408.

* * * * *